United States Patent
Mathur et al.

(10) Patent No.: US 10,376,704 B2
(45) Date of Patent: Aug. 13, 2019

(54) EXTERNAL PULSE GENERATOR DEVICE AND ASSOCIATED METHODS FOR TRIAL NERVE STIMULATION

(71) Applicant: Axonics Modulation Technologies, Inc., Irvine, CA (US)

(72) Inventors: Prabodh Mathur, Laguna, CA (US); Dennis Schroeder, Irvine, CA (US); John Woock, Costa Mesa, CA (US)

(73) Assignee: AXONICS MODULATION TECHNOLOGIES, INC., Irvine, CA (US)

( * ) Notice: Subject to any disclaimer, the term of this patent is extended or adjusted under 35 U.S.C. 154(b) by 0 days.

(21) Appl. No.: 15/431,475

(22) Filed: Feb. 13, 2017

(65) Prior Publication Data

US 2017/0239483 A1    Aug. 24, 2017

Related U.S. Application Data

(60) Provisional application No. 62/294,639, filed on Feb. 12, 2016.

(51) Int. Cl.
*A61N 1/00* (2006.01)
*A61N 1/378* (2006.01)
(Continued)

(52) U.S. Cl.
CPC .......... *A61N 1/3787* (2013.01); *A61N 1/0502* (2013.01); *A61N 1/0558* (2013.01);
(Continued)

(58) Field of Classification Search
CPC .............. A61N 1/3787; A61N 1/37241; A61N 1/0502; A61N 1/0558; A61N 1/37235–37247
See application file for complete search history.

(56) References Cited

U.S. PATENT DOCUMENTS

| | | |
|---|---|---|
| 3,646,940 A | 3/1972 | Timm et al. |
| 4,019,518 A | 4/1977 | Sorenson et al. |

(Continued)

FOREIGN PATENT DOCUMENTS

| | | |
|---|---|---|
| EP | 1680182 A1 | 7/2006 |
| EP | 1680182 B1 | 7/2006 |

(Continued)

OTHER PUBLICATIONS

Bosch et al., Sacral (S3) Segmental Nerve Stimulation as a Treatment for Urge Incontinence in Patients with Detrusor Instability: Results of Chronic Electrical Stimulation Using an Implantable Neural Prosthesis, The Journal of Urology, vol. 154, Aug. 1995, pp. 504-507.

Ghovanloo et al., A Small Size Large Voltage Compliance Programmable Current Source for Biomedical Implantable Microstimulators, Proceedings of the 25th Annual International Conference of the IEEE EMBS, Sep. 17-21, 2003, pp. 1979-1982.

(Continued)

*Primary Examiner* — Scott M. Getzow

(74) *Attorney, Agent, or Firm* — Kilpatrick Townsend and Stockton LLP

(57) ABSTRACT

Systems and methods for providing a trial neurostimulation to a patient for assesssing suitability of a permanently implanted neurostimulation are provided herein. In one aspect, a trial neurostimulation system includes an EPG affixation device that secures the EPG to the patient when connected to a lead extending through a percutaneous incission to a target tissue location, while allowing for ready removal of the EPG for charging or bathing. In another aspect, the system includes an EPG provided with a multi-purpose connector rectacle through which the EPG can deliver neurostimulation therapy to an implanted lead or the EPG can be charged. In yet another aspect, the EPG can include a multi-purpose connector receptacle that is alternatingly connectable with a plurality of differing connector to faciltiate differing types of therapies with one or more (Continued)

neurostimulation devices, ground patches or various other devices, such as charging or testing devices.

24 Claims, 16 Drawing Sheets

(51) Int. Cl.
    *A61N 1/05*     (2006.01)
    *A61N 1/372*     (2006.01)
    *A61N 1/375*     (2006.01)
    *A61N 1/36*     (2006.01)

(52) U.S. Cl.
    CPC ......... *A61N 1/36017* (2013.01); *A61N 1/375* (2013.01); *A61N 1/37241* (2013.01); *A61N 1/3603* (2017.08); *A61N 1/3752* (2013.01)

(56) References Cited

U.S. PATENT DOCUMENTS

| | | | |
|---|---|---|---|
| 4,044,774 A | 8/1977 | Corbin et al. | |
| 4,340,062 A | 7/1982 | Thompson et al. | |
| 4,553,702 A | 11/1985 | Coffee et al. | |
| 4,558,702 A | 12/1985 | Barreras et al. | |
| 4,744,371 A | 5/1988 | Harris et al. | |
| 5,690,693 A | 11/1997 | Wang et al. | |
| 5,702,428 A | 12/1997 | Tippey et al. | |
| 5,702,431 A | 12/1997 | Wang et al. | |
| 5,735,887 A | 4/1998 | Barreras | |
| 5,741,316 A | 4/1998 | Chen et al. | |
| 5,876,423 A | 3/1999 | Braun et al. | |
| 5,974,344 A | 10/1999 | Shoemaker | |
| 6,027,456 A | 2/2000 | Feler et al. | |
| 6,035,237 A | 3/2000 | Schulman et al. | |
| 6,052,624 A | 4/2000 | Mann et al. | |
| 6,055,456 A | 4/2000 | Gerber | |
| 6,057,513 A | 5/2000 | Tsuruta et al. | |
| 6,067,474 A | 5/2000 | Schulman et al. | |
| 6,076,017 A | 6/2000 | Taylor et al. | |
| 6,104,960 A | 8/2000 | Duysens et al. | |
| 6,172,556 B1 | 1/2001 | Prentice et al. | |
| 6,178,353 B1 | 1/2001 | Griffith et al. | |
| 6,191,365 B1 | 2/2001 | Avellanet et al. | |
| 6,208,894 B1 | 3/2001 | Schulman et al. | |
| 6,212,431 B1 | 4/2001 | Hahn et al. | |
| 6,221,513 B1 | 4/2001 | Lasater et al. | |
| 6,246,911 B1 | 6/2001 | Seligman | |
| 6,249,703 B1 | 6/2001 | Stanton et al. | |
| 6,265,789 B1 | 7/2001 | Hayakawa et al. | |
| 6,306,100 B1 | 10/2001 | Prass et al. | |
| 6,315,721 B2 | 11/2001 | Schulman et al. | |
| 6,354,991 B1 | 3/2002 | Gross et al. | |
| 6,360,750 B1 | 3/2002 | Gerber et al. | |
| 6,393,325 B1 | 5/2002 | Mann et al. | |
| 6,438,423 B1 | 8/2002 | Rezai et al. | |
| 6,442,434 B1 | 8/2002 | Zarinetchi et al. | |
| 6,466,817 B1 | 10/2002 | Kaula et al. | |
| 6,505,075 B1 | 1/2003 | Weiner et al. | |
| 6,516,227 B1 | 2/2003 | Mann et al. | |
| 6,584,355 B2 | 6/2003 | Stessman et al. | |
| 6,600,954 B2 | 7/2003 | Cohen et al. | |
| 6,609,031 B1 | 8/2003 | Law et al. | |
| 6,609,032 B1 | 8/2003 | Woods et al. | |
| 6,652,449 B1 | 11/2003 | Gross et al. | |
| 6,662,051 B1 | 12/2003 | Eraker et al. | |
| 6,721,603 B2 | 4/2004 | Zabara et al. | |
| 6,735,474 B1 | 5/2004 | Loeb et al. | |
| 6,745,077 B1 | 6/2004 | Griffith et al. | |
| 6,809,701 B2 | 10/2004 | Amundson et al. | |
| 6,836,684 B1 | 12/2004 | Rijkhoff et al. | |
| 6,847,849 B2 | 1/2005 | Mamo et al. | |
| 6,892,098 B2 | 5/2005 | Ayal et al. | |
| 6,895,280 B2 | 5/2005 | Meadows et al. | |
| 6,896,651 B2 | 5/2005 | Gross et al. | |
| 6,901,287 B2 | 5/2005 | Davis et al. | |
| 6,941,171 B2 | 9/2005 | Mann et al. | |
| 6,971,393 B1 | 12/2005 | Mamo et al. | |
| 6,989,200 B2 | 1/2006 | Schnittgrund et al. | |
| 6,990,376 B2 | 1/2006 | Tanagho et al. | |
| 6,999,819 B2 | 2/2006 | Swoyer et al. | |
| 7,051,419 B2 | 5/2006 | Robinson et al. | |
| 7,054,689 B1 | 5/2006 | Whitehurst et al. | |
| 7,069,081 B2 | 6/2006 | Biggs et al. | |
| 7,127,298 B1 | 10/2006 | He et al. | |
| 7,142,925 B1 | 11/2006 | Bhadra et al. | |
| 7,146,219 B2 | 12/2006 | Sieracki et al. | |
| 7,151,914 B2 | 12/2006 | Brewer et al. | |
| 7,167,749 B2 | 1/2007 | Biggs et al. | |
| 7,167,756 B1 | 1/2007 | Torgerson et al. | |
| 7,177,690 B2 | 2/2007 | Thacker et al. | |
| 7,177,698 B2 | 2/2007 | Park et al. | |
| 7,181,286 B2 | 2/2007 | Sieracki et al. | |
| 7,187,978 B2 | 3/2007 | Malek et al. | |
| 7,191,005 B2 | 3/2007 | Stessman et al. | |
| 7,212,110 B1 | 5/2007 | Martin et al. | |
| 7,225,032 B2 | 5/2007 | Schmeling et al. | |
| 7,231,254 B2 | 6/2007 | DiLorenzo | |
| 7,234,853 B2 | 6/2007 | Givoletti | |
| 7,245,972 B2 | 7/2007 | Davis et al. | |
| 7,286,880 B2 | 10/2007 | Olson et al. | |
| 7,305,268 B2 | 12/2007 | Gliner et al. | |
| 7,317,948 B1 | 1/2008 | King et al. | |
| 7,324,852 B2 | 1/2008 | Barolat et al. | |
| 7,324,853 B2 | 1/2008 | Ayal et al. | |
| 7,328,068 B2 | 2/2008 | Spinelli et al. | |
| 7,330,764 B2 | 2/2008 | Swoyer et al. | |
| 7,359,751 B1 | 4/2008 | Erickson et al. | |
| 7,369,894 B2 | 5/2008 | Gerber et al. | |
| 7,386,348 B2 | 6/2008 | Fowler et al. | |
| 7,387,603 B2 | 6/2008 | Gross et al. | |
| 7,396,265 B2 | 7/2008 | Darley et al. | |
| 7,415,308 B2 | 8/2008 | Gerber et al. | |
| 7,444,181 B2 | 10/2008 | Doan et al. | |
| 7,450,991 B2 | 11/2008 | Smith et al. | |
| 7,460,911 B2 | 12/2008 | Cosendai et al. | |
| 7,463,928 B2 | 12/2008 | Torgerson et al. | |
| 7,470,236 B1 | 12/2008 | Marino et al. | |
| 7,483,752 B2 | 1/2009 | Von Arx et al. | |
| 7,496,404 B2 | 2/2009 | Woods et al. | |
| 7,515,967 B2 | 4/2009 | Phillips et al. | |
| 7,532,936 B2 | 5/2009 | Erickson et al. | |
| 7,539,538 B2 | 5/2009 | Nimmagadda et al. | |
| 7,551,960 B2 | 6/2009 | Forsberg et al. | |
| 7,555,346 B1 | 6/2009 | Loeb et al. | |
| 7,565,203 B2 | 7/2009 | Greenberg et al. | |
| 7,578,819 B2 | 8/2009 | Bleich et al. | |
| 7,580,752 B2 | 8/2009 | Gerber et al. | |
| 7,582,053 B2 | 9/2009 | Gross et al. | |
| 7,617,002 B2 | 11/2009 | Goetz et al. | |
| 7,640,059 B2 | 12/2009 | Forsberg et al. | |
| 7,643,880 B2 | 1/2010 | Tanagho et al. | |
| 7,706,889 B2 | 4/2010 | Gerber et al. | |
| 7,720,547 B2 | 5/2010 | Denker et al. | |
| 7,725,191 B2 | 5/2010 | Greenberg et al. | |
| 7,734,355 B2 | 6/2010 | Cohen et al. | |
| 7,738,963 B2 | 6/2010 | Hickman et al. | |
| 7,738,965 B2 | 6/2010 | Phillips et al. | |
| 7,747,330 B2 | 6/2010 | Nolan et al. | |
| 7,771,838 B1 | 8/2010 | Colvin et al. | |
| 7,774,069 B2 | 8/2010 | Olson et al. | |
| 7,801,619 B2 | 9/2010 | Gerber et al. | |
| 7,813,803 B2 | 10/2010 | Heruth et al. | |
| 7,813,809 B2 | 10/2010 | Strother et al. | |
| 7,826,901 B2 | 11/2010 | Torgerson et al. | |
| 7,848,818 B2 | 12/2010 | Barolat et al. | |
| 7,904,167 B2 | 3/2011 | Park et al. | |
| 7,912,555 B2 | 3/2011 | Swoyer et al. | |
| 7,925,357 B2 | 4/2011 | Phillips et al. | |
| 7,932,696 B2 | 4/2011 | Peterson et al. | |
| 7,933,656 B2 | 4/2011 | Sieracki et al. | |
| 7,935,051 B2 | 5/2011 | Blewett et al. | |
| 7,937,158 B2 | 5/2011 | Erickson et al. | |
| 7,952,349 B2 | 5/2011 | Bono et al. | |

(56) References Cited

U.S. PATENT DOCUMENTS

| | | |
|---|---|---|
| 7,957,818 B2 | 6/2011 | Swoyer et al. |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Blewett et al. |
| 8,000,805 B2 | 8/2011 | Swoyer et al. |
| 8,005,535 B2 | 8/2011 | Blewett et al. |
| 8,005,549 B2 | 8/2011 | Seifert et al. |
| 8,005,550 B2 | 8/2011 | Seifert et al. |
| 8,019,423 B2 | 9/2011 | Possover et al. |
| 8,024,047 B2 | 9/2011 | Olson et al. |
| 8,036,756 B2 | 10/2011 | Swoyer et al. |
| 8,044,635 B2 | 10/2011 | Peterson et al. |
| 8,050,769 B2 | 11/2011 | Blewett et al. |
| 8,055,337 B2 | 11/2011 | Moffitt et al. |
| 8,068,912 B2 | 11/2011 | Gharib et al. |
| 8,083,663 B2 | 12/2011 | Gross et al. |
| 8,103,360 B2 | 1/2012 | Foster et al. |
| 8,116,862 B2 | 2/2012 | Stevenson et al. |
| 8,121,701 B2 | 2/2012 | Loeb et al. |
| 8,129,942 B2 | 3/2012 | Choi et al. |
| 8,131,358 B2 | 3/2012 | Moffitt et al. |
| 8,140,167 B2 | 3/2012 | Donders et al. |
| 8,140,168 B2 | 3/2012 | Olson et al. |
| 8,145,324 B1 | 3/2012 | Stevenson et al. |
| 8,150,530 B2 | 4/2012 | Wesselink et al. |
| 8,175,717 B2 | 5/2012 | Feldman et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson et al. |
| 8,219,202 B2 | 7/2012 | Giftakis et al. |
| 8,233,990 B2 | 7/2012 | Goetz et al. |
| 8,255,057 B2 | 8/2012 | Fang et al. |
| 8,311,636 B2 | 11/2012 | Gerber et al. |
| 8,314,594 B2 | 11/2012 | Scott et al. |
| 8,332,040 B1 | 12/2012 | Winstrom et al. |
| 8,340,786 B2 | 12/2012 | Gross et al. |
| 8,362,742 B2 | 1/2013 | Kallmyer et al. |
| 8,369,943 B2 | 2/2013 | Shuros et al. |
| 8,382,059 B2 | 2/2013 | Le Gette et al. |
| 8,386,048 B2 | 2/2013 | Fister et al. |
| 8,417,346 B2 | 4/2013 | Giftakis et al. |
| 8,423,146 B2 | 4/2013 | Giftakis et al. |
| 8,447,402 B1 | 5/2013 | Antalfy et al. |
| 8,447,408 B2 | 5/2013 | North et al. |
| 8,452,409 B2 | 5/2013 | Bachinski et al. |
| 8,457,756 B2 | 6/2013 | Rahman et al. |
| 8,457,758 B2 | 6/2013 | Olson et al. |
| 8,480,437 B2 | 7/2013 | Cook et al. |
| 8,494,625 B2 | 7/2013 | Hargrove et al. |
| 8,515,545 B2 | 8/2013 | Trier et al. |
| 8,538,530 B1 | 9/2013 | Orinski |
| 8,543,223 B2 | 9/2013 | Geroy et al. |
| 8,549,015 B2 | 10/2013 | Barolat et al. |
| 8,554,322 B2 | 10/2013 | Olson et al. |
| 8,555,894 B2 | 10/2013 | Schulman et al. |
| 8,562,539 B2 | 10/2013 | Marino et al. |
| 8,571,677 B2 | 10/2013 | Torgerson et al. |
| 8,577,474 B2 | 11/2013 | Feldman et al. |
| 8,583,253 B1 | 11/2013 | Shi et al. |
| 8,588,917 B2 | 11/2013 | Whitehurst et al. |
| 8,620,454 B2 | 12/2013 | Bolea et al. |
| 8,626,314 B2 | 1/2014 | Swoyer et al. |
| 8,644,933 B2 | 2/2014 | Ozawa et al. |
| 8,655,451 B2 | 2/2014 | Park et al. |
| 8,655,453 B2 | 2/2014 | Werder et al. |
| 8,700,175 B2 | 4/2014 | Fell et al. |
| 8,700,177 B2 | 4/2014 | Strother et al. |
| 8,706,254 B2 | 4/2014 | Mcclure et al. |
| 8,725,262 B2 | 5/2014 | Olson et al. |
| 8,725,269 B2 | 5/2014 | Nolan et al. |
| 8,738,138 B2 | 5/2014 | Fundeburk et al. |
| 8,738,141 B2 | 5/2014 | Smith et al. |
| 8,738,148 B2 | 5/2014 | Olson et al. |
| 8,750,985 B2 | 6/2014 | Nimmagadda et al. |
| 8,761,897 B2 | 6/2014 | Kaula et al. |
| 8,768,452 B2 | 7/2014 | Gerber et al. |
| 8,774,912 B2 | 7/2014 | Gerber et al. |
| 8,774,924 B2 | 7/2014 | Weiner et al. |
| 8,774,942 B2 | 7/2014 | Lund et al. |
| 8,805,524 B2 | 8/2014 | Loeb et al. |
| 8,892,217 B2 | 11/2014 | Camps et al. |
| 8,918,174 B2 | 12/2014 | Peterson et al. |
| 8,954,148 B2 | 2/2015 | Cottrill et al. |
| 8,989,861 B2 | 3/2015 | Nelson et al. |
| 9,050,473 B2 | 6/2015 | Loeb et al. |
| 9,089,712 B2 | 7/2015 | Joshi et al. |
| 9,108,063 B2 | 8/2015 | Olson et al. |
| 9,149,635 B2 | 10/2015 | Denison et al. |
| 9,155,885 B2 | 10/2015 | Miesel et al. |
| 9,166,321 B2 | 10/2015 | Smith et al. |
| 9,168,374 B2 | 10/2015 | Su |
| 9,192,763 B2 | 11/2015 | Gerber et al. |
| 9,197,173 B2 | 11/2015 | Denison et al. |
| 9,205,255 B2 | 12/2015 | Strother et al. |
| 9,209,634 B2 | 12/2015 | Cottrill et al. |
| 9,216,294 B2 | 12/2015 | Bennett et al. |
| 9,227,076 B2 | 1/2016 | Sharma et al. |
| 9,238,135 B2 | 1/2016 | Goetz et al. |
| 9,240,630 B2 | 1/2016 | Joshi |
| 9,242,090 B2 | 1/2016 | Atalar et al. |
| 9,244,898 B2 | 1/2016 | Mcclure et al. |
| 9,248,292 B2 | 2/2016 | Trier et al. |
| 9,259,578 B2 | 2/2016 | Torgerson et al. |
| 9,259,582 B2 | 2/2016 | Floyd et al. |
| 9,265,958 B2 | 2/2016 | Joshi et al. |
| 9,270,134 B2 | 2/2016 | Gaddam et al. |
| 9,272,140 B2 | 3/2016 | Gerber et al. |
| 9,283,394 B2 | 3/2016 | Whitehurst et al. |
| 9,295,851 B2 | 3/2016 | Gordon et al. |
| 9,308,022 B2 | 4/2016 | Chitre et al. |
| 9,314,616 B2 | 4/2016 | Wells et al. |
| 9,320,899 B2 | 4/2016 | Parramon et al. |
| 9,352,148 B2 | 5/2016 | Stevenson et al. |
| 9,352,150 B2 | 5/2016 | Stevenson et al. |
| 9,358,039 B2 | 6/2016 | Kimmel et al. |
| 9,364,658 B2 | 6/2016 | Wechter |
| 9,517,338 B1 * | 12/2016 | Jiang ................ A61N 1/08 |
| 2002/0016617 A1 | 2/2002 | Oldham |
| 2003/0040291 A1 | 2/2003 | Brewer |
| 2005/0104577 A1 | 5/2005 | Matei et al. |
| 2006/0041283 A1 | 2/2006 | Gelfand et al. |
| 2006/0142822 A1 | 6/2006 | Tulgar et al. |
| 2006/0206166 A1 | 9/2006 | Weiner et al. |
| 2007/0060980 A1 | 3/2007 | Strother et al. |
| 2007/0265675 A1 | 11/2007 | Lund et al. |
| 2007/0293914 A1 | 12/2007 | Woods et al. |
| 2008/0081962 A1 | 4/2008 | Miller et al. |
| 2008/0161874 A1 * | 7/2008 | Bennett ............ A61N 1/36007 607/39 |
| 2008/0183236 A1 | 7/2008 | Gerber et al. |
| 2009/0105693 A1 * | 4/2009 | Ben-David ........ A61B 17/3401 604/537 |
| 2009/0118796 A1 | 5/2009 | Chen et al. |
| 2010/0076254 A1 | 3/2010 | Jimenez et al. |
| 2010/0076534 A1 | 3/2010 | Mock et al. |
| 2011/0152987 A1 | 6/2011 | Wahlgren et al. |
| 2011/0251662 A1 | 10/2011 | Griswold et al. |
| 2011/0282416 A1 | 11/2011 | Hamann et al. |
| 2011/0301667 A1 | 12/2011 | Olson et al. |
| 2011/0313427 A1 | 12/2011 | Gindele et al. |
| 2011/0319947 A1 | 12/2011 | Chun et al. |
| 2012/0041512 A1 | 2/2012 | Weiner et al. |
| 2012/0046712 A1 | 2/2012 | Woods et al. |
| 2012/0071951 A1 | 3/2012 | Swanson |
| 2012/0130448 A1 | 5/2012 | Woods et al. |
| 2012/0139485 A1 | 6/2012 | Olson et al. |
| 2012/0235634 A1 | 9/2012 | Hall et al. |
| 2012/0276854 A1 | 11/2012 | Joshi et al. |
| 2012/0276856 A1 | 11/2012 | Joshi et al. |

(56) References Cited

U.S. PATENT DOCUMENTS

| | | |
|---|---|---|
| 2013/0004925 A1 | 1/2013 | Labbe et al. |
| 2013/0006330 A1 | 1/2013 | Wilder et al. |
| 2013/0006331 A1 | 1/2013 | Weisgarber et al. |
| 2013/0150925 A1 | 6/2013 | Vamos et al. |
| 2013/0172956 A1 | 7/2013 | Goddard et al. |
| 2013/0197608 A1 | 8/2013 | Eiger et al. |
| 2013/0207863 A1 | 8/2013 | Joshi |
| 2013/0310630 A1 | 11/2013 | Smith et al. |
| 2013/0310894 A1 | 11/2013 | Trier et al. |
| 2013/0325097 A1 | 12/2013 | Loest |
| 2013/0331909 A1 | 12/2013 | Gerber et al. |
| 2014/0106617 A1* | 4/2014 | Csak .................... H01R 13/504 439/606 |
| 2014/0107743 A1 | 4/2014 | Wahlstrand et al. |
| 2014/0194948 A1 | 7/2014 | Strother et al. |
| 2014/0207220 A1 | 7/2014 | Boling et al. |
| 2014/0222112 A1 | 8/2014 | Fell et al. |
| 2014/0237806 A1 | 8/2014 | Smith et al. |
| 2014/0243926 A1* | 8/2014 | Carcieri ............. A61N 1/36071 607/46 |
| 2014/0277270 A1 | 9/2014 | Parramon et al. |
| 2015/0028798 A1 | 1/2015 | Dearden et al. |
| 2015/0088227 A1 | 3/2015 | Shishilla et al. |
| 2015/0094790 A1 | 4/2015 | Shishilla et al. |
| 2015/0100106 A1* | 4/2015 | Shishilla .............. A61N 1/3752 607/59 |
| 2015/0134027 A1 | 5/2015 | Kaula et al. |
| 2015/0214604 A1 | 7/2015 | Zhao et al. |
| 2015/0231402 A1 | 8/2015 | Aghassian |
| 2015/0335893 A1 | 11/2015 | Parker |
| 2016/0022996 A1 | 1/2016 | Kaula et al. |
| 2016/0045745 A1 | 2/2016 | Mathur et al. |

FOREIGN PATENT DOCUMENTS

| | | |
|---|---|---|
| EP | 1904153 B1 | 4/2008 |
| EP | 2243509 A1 | 10/2010 |
| EP | 2731673 | 5/2014 |
| WO | WO 2000/056677 A1 | 9/2000 |
| WO | WO 2008/021524 A2 | 2/2008 |
| WO | WO 2011/059565 A1 | 5/2011 |
| WO | WO 2014/087337 A1 | 6/2014 |
| WO | WO 2016/097731 A2 | 6/2016 |

OTHER PUBLICATIONS

Tanagho et al., Bladder Pacemaker: Scientific Basis and Clinical Future, Urology, vol. 20, No. 6, Dec. 1982, pp. 614-619.
U.S. Appl. No. 14/827,067, filed Aug. 14, 2015.
U.S. Appl. No. 14/827,074, filed Aug. 14, 2015.
U.S. Appl. No. 14/827,081, filed Aug. 14, 2015.
U.S. Appl. No. 14/827,095, filed Aug. 14, 2015.
U.S. Appl. No. 14/827,108, filed Aug. 14, 2015.
U.S. Appl. No. 14/991,649, filed Jan. 8, 2016.
U.S. Appl. No. 14/991,752, filed Jan. 8, 2016.
U.S. Appl. No. 14/991,784, filed Jan. 8, 2016.
U.S. Appl. No. 62/101,782, filed Jan. 9, 2015.
U.S. Appl. No. 62/038,122, filed Aug. 15, 2014.
U.S. Appl. No. 62/101,666, filed Jan. 9, 2015.
U.S. Appl. No. 62/101,884, filed Jan. 9, 2015.
U.S. Appl. No. 62/101,897, filed Jan. 9, 2015.
U.S. Appl. No. 62/101,899, filed Jan. 9, 2015.
U.S. Appl. No. 62/110,274, filed Jan. 30, 2015.
U.S. Appl. No. 62/191,134, filed Jul. 10, 2015.
U.S. Appl. No. 62/101,888, filed Jan. 9, 2015.

* cited by examiner

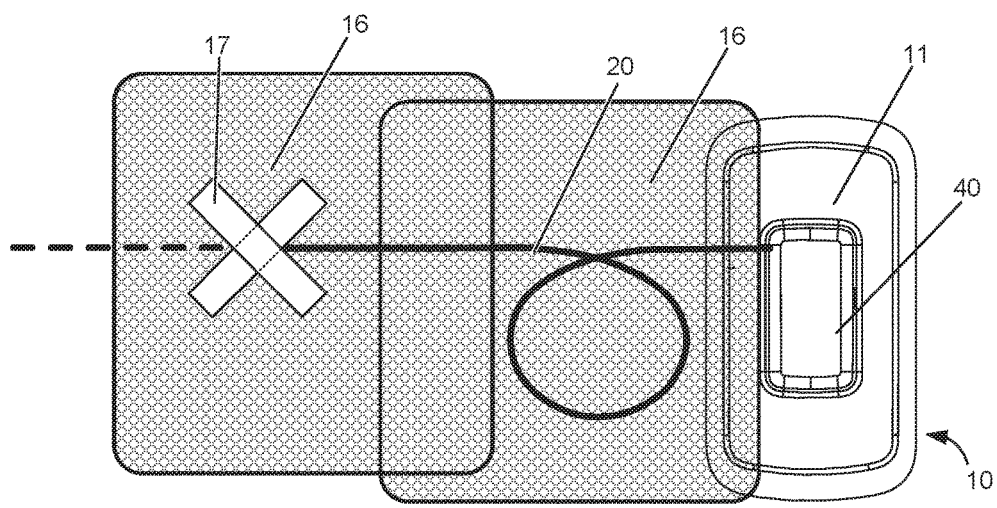
FIG. 3C
FIG. 4A
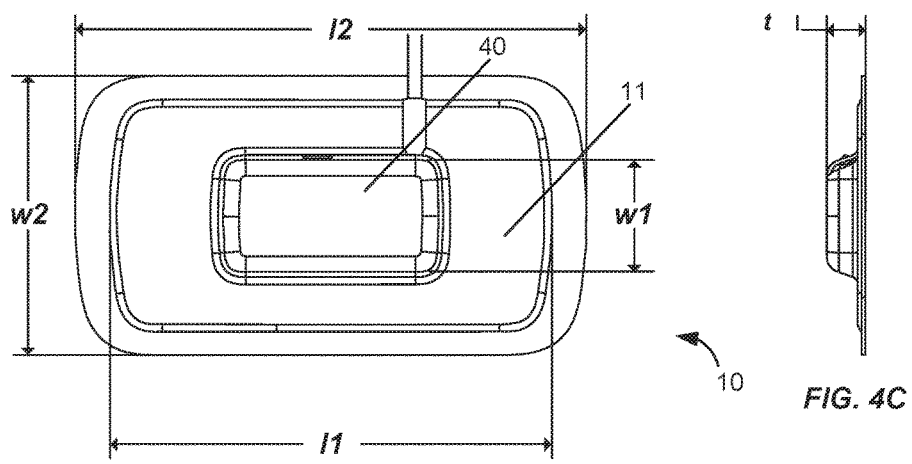
FIG. 4B
FIG. 4C

EXTERNAL PULSE GENERATOR DEVICE AND ASSOCIATED METHODS FOR TRIAL NERVE STIMULATION

CROSS-REFERENCES TO RELATED APPLICATIONS

This application claims the benefit of priority to U.S. Provisional Application 62/294,639 filed Feb. 12, 2016, the entire contents of which are incorporated herein by reference.

The present application is related to U.S. Non-Provisional application Ser. No. 14/827,081, entitled External Pulse Generator Device and Associated Methods for Trial Nerve Stimulation" filed on Aug. 14, 2015, the entire contents of which are incorporated herein by reference in its entirety for all purposes.

BACKGROUND OF THE INVENTION

Treatments with implanted neurostimulation systems have become increasingly more common in recent years. While such systems have shown promise in treating a number of chronic conditions, effectiveness of treatment may vary considerably between patients and viability of treatment can be difficult to determine before implantation. Although conventional methods of implantation often utilize preliminary testing with a temporary, partly implanted neurostimulation systems to assess viability of treatment, such systems may not provide an accurate representation of treatment with a fully implanted device. In addition, such systems are often bulky, uncomfortable and limit patient mobility, such that many patients elect not to receive a temporary system or a fully implanted system. In addition, many such temporary partly implanted systems may not operate in the same manner as their fully implanted counterparts due to differences between pulse generators or changes in position of the neurostimulation leads during conversion. Therefore, it is desirable to provide methods and devices for providing trial treatment systems that provide a more accurate representation of treatment, improve patient comfort and provide consistent treatment outcomes as compared to fully implanted neurostimulation systems.

BRIEF SUMMARY OF THE INVENTION

The present invention relates to neurostimulation treatment systems, and in particular a neurostimulation treatment system having an EPG with a multi-purpose connector receptacle and affixation devices on which the EPG is releasably mounted and that are secured to the patient during a trial neurostimulation treatment. Typically, such a trial neurostimulation treatment includes a partly implanted neurostimulation lead extending to an external pulse generator for conducting a trial neurostimulation treatment for assessing viability of a fully implanted system. In one aspect, the system includes a partly implanted neurostimulation lead that extends from one or more implanted neurostimulation electrodes to an external pulse generator (EPG) supported in an affixation device secured to the patient. In some aspects, the trial period may be as little as 4-7 days, while in other aspects the trial period may extend two weeks or more, typically about two weeks.

In one aspect, an external pulse generator is provided that includes an outer housing having at least one port and a connector receptacle accessed via the port. The receptacle can be adapted for receivably coupling with a proximal portion of an implantable neurostimulation lead to electrically couple the external pulse generator with one or more neurostimulation electrodes of the neurostimulation lead implanted at a target tissue. The external pulse generator further includes a pulse generator electrically coupled with the connector receptacle and adapted for generating neurostimulation pulses to one or more neurostimulation electrodes of the lead. The connector receptacle can be configured to support various types of neurostimulation lead, including a Peripheral Nerve Evaluation (PNE) lead (bilateral or unilateral) as well as a tined lead. The external pulse generator can further include a rechargeable battery electrically coupled to the pulse generator and connector receptacle that is configured for recharging by electrical power delivered via the connector receptacle.

In some embodiments, the external pulse generator can include electrical circuitry coupling each of the pulse generator, the rechargeable battery and the connector receptacle. The circuitry is configured, by programmable instructions recorded on a memory thereof, to power the pulse generator with the charged battery and charge the battery with electrical power delivered via the connector receptacle. The circuitry can further be configured to switch between differing operating modes of the external pulse generator, which can include a therapy mode and a charging mode. In some embodiments, the circuitry is configured to switch to the charging mode when the connector receptacle is coupled to power connector of a charging cord coupled to an external power source. The circuitry can also be configured to switch to the therapy mode when the connector receptacle is coupled to the proximal connector of the neurostimulation lead. The circuitry can further be adapted for suspending pulse generation in response to disconnecting the neurostimulation lead. Suspending pulse generation can be performed in response to a detection of loss of electrical connectivity within the connector receptacle while in the therapy mode. This capability serves as a safety feature and can be included in any EPG, including multi-port EPGs, regardless of whether a rechargeable or a permanent battery is used.

In some embodiments, an external pulse generators can include circuitry configured for switching to the charging mode by electrically connecting the battery to the receptacle while operatively disconnecting the battery from the pulse generator, and switching to the therapy mode by operatively connecting the pulse generator to the battery and electrically disconnecting the battery from the receptacle. In some embodiments, the external pulse generator includes one or more stimulation programs operable within the therapy mode for use in one or more trial stimulation periods. In some embodiments, the external pulse generator is reusable such that it can be reused in multiple trials and/or with multiple patients. These aspects allow for improved versatility and makes a trial nerve stimulation more accessible to a wide range of patient populations.

In another aspect, such a trial system can include an external pulse generator with a multi-purpose connector receptacle. Such an external pulse generator can be configured with a single connector receptacle. The connector receptacle can be adapted for alternatingly connecting with a plurality of differing connectors, which can include a proximal lead connector of a neurostimulation lead and a power connector of a charging cord. In some embodiments, the circuitry is adapted for charging the battery when the charging cord is electrically coupled with a standard 120 volt outlet. The differing types of connectors can further include multiple differing connectors associated with differing cable sets, each suited for a particular purpose. Such differing connectors can include a first connector on a proximal portion of the neurostimulation lead; a second connector coupled in parallel to each of a ground and one or more proximal connectors of one or more implantable neurostimulation leads each having one or more neurostimulation electrodes, typically one or two proximal connectors of one or two neurostimulation leads; a third connector coupled in parallel to two or more proximal connectors of neurostimulation leads; and a fourth connector coupled with a charging cord and adapted for use in charging a rechargeable battery of the external pulse generator.

In another aspect, methods of performing a neurostimulation treatment during a trial period are provided herein. Such a method can include, first, electrically coupling a neurostimulation lead to an external pulse generator, the lead including one or more neurostimulation electrodes implanted at or near a targeted tissue within the patient. The neurostimulation treatment can then be delivered to the one or more neurostimulation electrodes with the external pulse generator. To facilitate charging, a rechargeable battery of the external pulse generator can be electrically coupled with an external power source via the first receptacle port of the external pulse generator, after which the battery is charged with the external power source. In some embodiments, delivering the neurostimulation lead can be performed in a neurostimulation operating mode of the external pulse generator, while charging of the external pulse generator can be performed in a charging operating mode. Such methods can further include: switching to the neurostimulation mode upon connection of the neurostimulation lead; and switching to the charging mode upon connection of a charging cord connected to an external power source and/or grounding.

In yet another aspect, an external pulse generator affixation device for securing an external pulse generator on a patient is provided herein. Such affixation devices can include a substrate having a patient coupling feature disposed along a first side and a mounting portion disposed along a second side opposite the first side. The mounting portion can include a plurality of tabs that engage the external pulse generator along an outer perimeter thereof so as to releasably couple the external pulse generator with the substrate. The plurality of tabs can be dimensioned and arranged so that a majority of the outer perimeter remains exposed to allow a patient to readily detach the external pulse generator from the adhesive patch while coupled to the patient. In some embodiments, the tabs are dimensioned and arranged so that about ⅔ or more of the outer perimeter remains exposed, or so that about ⅘ or more of the outer perimeter remains exposed, or so that about 9/10 or more of the perimeter remains exposed. In embodiments where the EPG is of a substantially rectangular shape, the multiple tabs can be arranged such that at least two diagonally opposing corners, or even all four corners, of the substantially rectangular EPG are exposed so that the EPG can be removed by grasping and engaging the corners of the EPG while secured within the affixation device.

In some embodiments, the mounting portion is non-electrically conductive. Typically, the affixation device is without any electrodes or electrically conductive path by which stimulation can be delivered to a skin of the patient.

In some embodiments, the affixation device includes a mounting portion with multiple tabs that include at least two resiliently deflectable tabs, each having a retention feature that engages an outer housing of an external pulse generator so as to releasably secure the external pulse generator to the substrate. The retention features of each of the at least two deflectable tabs can be adapted to be received within corresponding retention features on opposite sides of the external pulse generator. In some embodiments, the retention features of each tab comprises a contoured or stepped portion of each tab and the retention feature of the external pulse generator includes a retention recess having a corresponding contour or stepped portion for receiving the retention features of the at least two tabs. When the external pulse generator is substantially rectangular in shape, the at least two resiliently deflectable tabs can be adapted to engage opposing sides of the external pulse generator along a length dimension of the external pulse generator. In some embodiments, the mounting portion can include at least two additional tabs that engage opposing sides of the external pulse generator along a width dimension. In some embodiments, the at least two deflectable tabs and/or the at least two additional tabs engage the external pulse generator along a mid-portion thereof so that the external pulse generator can be removed by grasping the exposed sides and/or corners and twisting the external pulse generator along one or more axes.

In some embodiments, the affixation device includes an EPG mounting portion with multiple tabs that include a first pair of deflectable tabs adapted to engage opposite sides of the external pulse generator along a first axis to constrain movement along the first axis and a second pair of deflectable tabs adapted to engage opposite sides of the external pulse generator along a second axis substantially orthogonal to the first axis to constrain movement along the second axis. The second pair of deflectable tabs can each include a retention feature that engages a corresponding retention feature of the external pulse generator to constrain movement along a third axis orthogonal to each of the first and second axis. In this aspect, the plurality of tabs, in combination, constrain movement of the external pulse generator relative the substrate in all three dimensions. The substrate can be substantially rigid or semi-rigid between the multiple tabs so as to maintain the relative position and orientations of the tabs.

In some embodiments, the patient coupling feature of the affixation device is a flexible adhesive patch having a pressure-sensitive adhesive with sufficient strength to support an external pulse generator mounted on the adhesive patch adhered to a skin of the patient. In other embodiments, the patient coupling feature is a clip having an elongate member extending along and separable from the substrate. The clip can be biased towards the substrate so that the device is securable by insertion of a portion of a garment or belt between the elongate member and the substrate. The elongate clip member can be pivotally coupled to the substrate and biased toward the substrate is loaded with a spring.

In another aspect, the EPG includes a pulse generator electrically configured for generating neurostimulation pulses along multiple stimulation channels, a battery electrically coupled to the pulse generator, an outer housing enclosing the pulse generator and battery, and a multi-pin connector electrically coupled with the pulse generator through an external cable extending from the housing. The multi-pin connector includes multiple pins that correspond to the multiple channels. In some embodiments, the external cable is permanently attached to the housing such that any electrical connections between the multi-pin connector and the pulse generator are permanently sealed. Typically, the external cable is between 1 inch and 12 inches in length. In some embodiments, the battery is non-removable by the patient. In some embodiments, the battery is non-rechargeable.

In some embodiments, the EPG includes an actuatable user interface feature, such as a button or switch, that is disposed on the housing and configured for initiating wireless communication with an external programmer when actuated. In some embodiments, the actuatable user interface is configured such that actuation while the pulse generator is off or in a hibernation state causes the EPG to be receptive to or initiate wireless communication with the external programmer for a pre-determined period of time, and operation or communication by the EPG remains unchanged when actuation occurs while the pulse generator is operating or communicating. The pre-determined period of time can be any suitable period of time, for example 30 seconds or more, typically about 60 to 90 seconds. In some embodiments, the EPG is configured such that if no communication is established with the external programmer during the pre-determined period of time, the EPG returns to a hibernation or off state. Typically, the EPG is wirelessly coupleable with a patient remote and configured to turn off stimulation during operation in response to a command received from the patient remote.

In some embodiments, the EPG further includes a status indicator interface disposed on the housing and configured to indicate status of: a communication between the EPG and an external programmer, an operating state, a battery level, an error state, or any combination thereof. In some embodiments, the EPG housing has opposing major faces, a contoured top surface and a flattened underside surface for placement against the patient when the EPG is worn during a trial period. In some embodiments, the status indicator interface and the actuatable user interface are disposed on the underside surface of the housing of the EPG.

In another aspect, the trial system includes an EPG having a multi-pin connector and multiple connectors selectively coupleable within the multi-pin connector. The multiple connectors including at least two of: a first connector on a proximal portion of the neurostimulation lead, a second connector coupled in parallel to each of a ground and one or more proximal connectors of one or more implantable neurostimulation leads, each having one or more neurostimulation electrodes on a distal portion thereof, and a third connector coupled in parallel to two or more proximal connectors of two or more neurostimulation leads. In some embodiments, the trial system includes one or more connector cables coupleable with the multi-pin connector and one or more neurostimulation leads. In some embodiments, the one or more connectors can include a lead extension cable extending between a corresponding multi-pin connector and at least one implantable lead connector having a receptacle configured for receiving a proximal lead connector of a fully implantable neurostimulation lead. In some embodiments, the one or more connectors include a multi-lead cable extending between a corresponding multi-pin connector and multiple lead connectors, each having a lead receptacle for coupling with a neurostimulation lead, and at least one ground connector for coupling with a ground patch.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIG. 3C is a detail of the neurostimulation system in FIG. 3.

FIGS. 4A-4C are overhead and side views of an example EPG affixation patch, in accordance with some embodiments.

DETAILED DESCRIPTION OF THE INVENTION

Neurostimulation has been used for many years to treat a variety of conditions, from chronic pain, to erectile dysfunction and various urinary dysfunctions. While neurostimulation has proven effective in many applications, effective therapy often relies on consistently delivering therapeutic activation by one or more neurostimulation electrodes to particular nerves or targeted regions with a pulse generator. In recent years, fully implantable neurostimulation have become increasingly more commonplace. Although such implantable systems provide patients with greater freedom and mobility, the neurostimulation electrodes of such systems are more difficult to adjust once they are implanted. The neurostimulation electrodes are typically provided on a distal end of an implantable lead that is advanced through a tunnel formed in a patient tissue.

Figure 1:
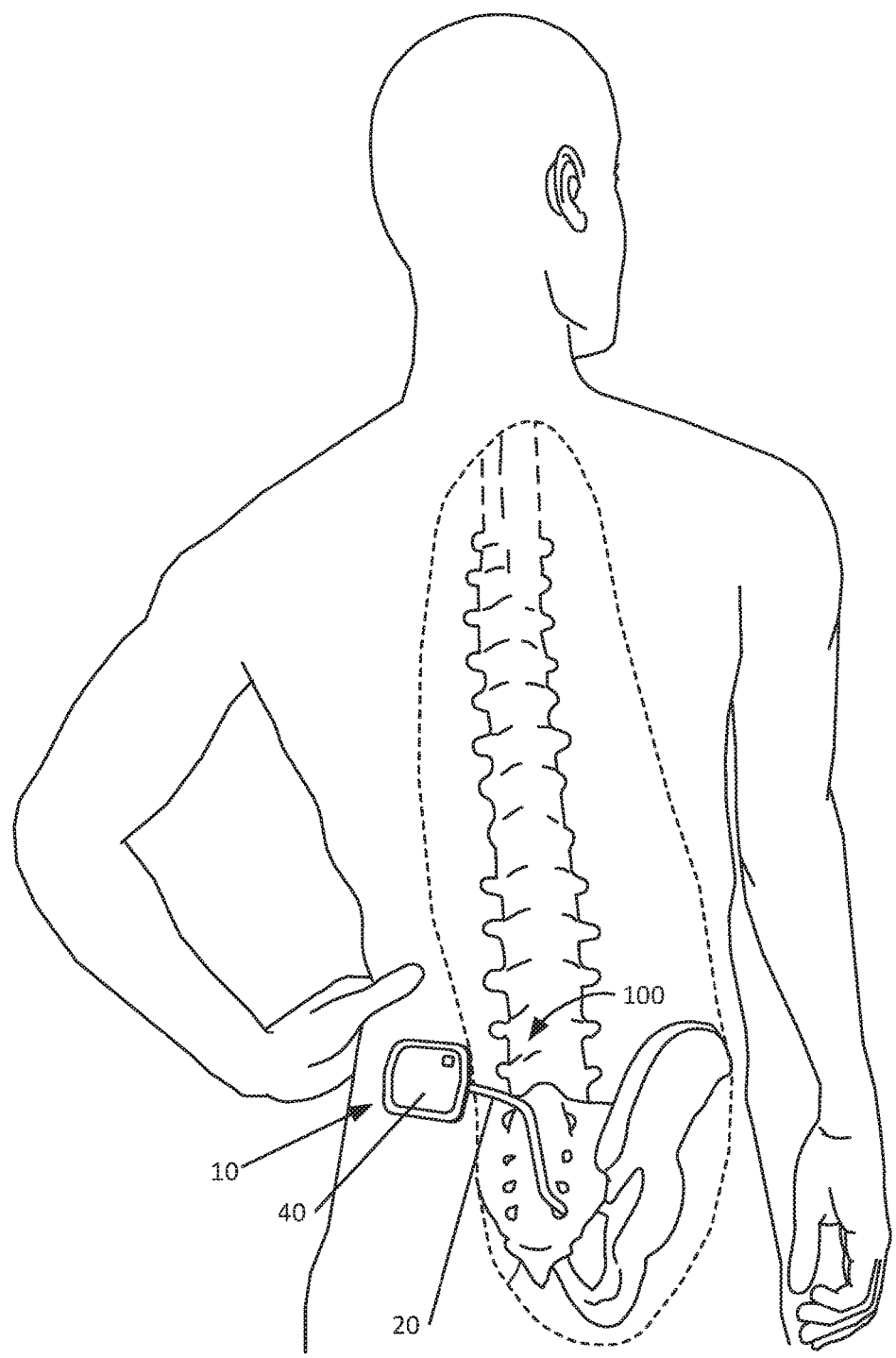
FIG. 1 is a schematic illustration of a trial neurostimulation system having a partly implanted lead extending to an EPG patch adhered to the skin of the patient, in accordance with some embodiments of the invention.

FIG. 1 schematically illustrates a use of a trial neurostimulation system utilizing an EPG affixation device, in accordance with aspect of the invention. Such a trial neurostimulation system can be used to assess viability of a fully implantable neurostimulation system. Implantable neurostimulation systems can be used in treating patients with, for example, chronic, severe, refractory neuropathic pain originating from peripheral nerves or various urinary and bowel dysfunctions. Implantable neurostimulation systems can be used to either stimulate a target peripheral nerve or the posterior epidural space of the spine. An implantable neurostimulation system includes an implanted pulse generator, typically implanted in a lower back region. In some embodiments, the pulse generator can generate one or more non-ablative electrical pulses that are delivered to a nerve to control pain or cause some other desired effect. In some applications, the pulses having a pulse amplitude of between 0-1,000 mA, 0-100 mA, 0-50 mA, 0-25 mA, and/or any other or intermediate range of amplitudes may be used. One or more of the pulse generators can include a processor and/or memory adapted to provide instructions to and receive information from the other components of the implantable neurostimulation system. The processor can include a microprocessor, such as a microprocessor from Intel® or Advanced Micro Devices, Inc.®, or the like. An implantable pulse generator may implement an energy storage feature, such as one or more capacitors or a battery, and typically includes a wireless charging unit.

The electrical pulses generated by the pulse generator are delivered to one or more nerves and/or to a target location via one or more leads that include one or more neurostimulation electrodes at or near the distal end. The leads can have a variety of shapes, can be a variety of sizes, and can be made from a variety of materials, which size, shape, and materials can be dictated by the application or other factors. In some applications, the leads may be implanted to extend along the spine or through one of the foramen of the sacrum, such as shown in FIG. 1, such as in sacral nerve stimulation. In other applications, the leads may be implanted in a peripheral portion of the patient's body, such as in the arms or legs, and can be configured to deliver one or more electrical pulses to the peripheral nerve such as may be used to relieve chronic pain.

One or more properties of the electrical pulses can be controlled via a controller of the implanted pulse generator. In some embodiments, these properties can include, for example, the frequency, strength, pattern, duration, or other aspects of the timing and magnitude of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 1, the implantable neurostimulation system 100 includes a controller in the implantable pulse generator having one or more pulse programs, plans, or patterns and/or to select one or more of the created pulse programs, plans, or patterns.

Sacral neuromodulation (SNM), also known as sacral nerve stimulation (SNS), is defined as the delivery of mild electrical pulses to the sacral nerve to modulate the neural pathways controlling bladder and rectal function. This policy addresses use of SNM in the treatment of urinary or fecal incontinence, urinary or fecal nonobstructive retention, or chronic pelvic pain in patients with intact neural innervation of the bladder and/or rectum.

Treatment using SNM, also known as SNS, is one of several alternative modalities for patients with fecal incontinence,r overactive bladder (urge incontinence, significant symptoms of urgency-frequency) or nonobstructive urinary retention who have failed behavioral (e.g., prompted voiding) and/or pharmacologic therapies. Urge incontinence is defined as leakage of urine when there is a strong urge to void. Urgency-frequency is an uncontrollable urge to urinate, resulting in very frequent small volumes. Urinary retention is the inability to completely empty the bladder of urine. Fecal incontinence is the inability to control bowel movements resulting in unexpected leakage of fecal matter.

The SNM device consists of an implantable pulse generator that delivers controlled electrical impulses. This pulse generator is attached to wire leads that connect to the sacral nerves, most commonly the S3 nerve root. Two external components of the system help control the electrical stimulation. A patient remote control may be kept by the patient and can be used to control any of the variety of operational aspects of the EPG and its stimulation parameters. In one such embodiment, the patient remote control may be used to turn the device on or return the EPG to a hibernation state or to adjust stimulation intensity. A console programmer is kept by the physician and used to adjust the settings of the pulse generator.

In a conventional approach, prior to implantation of the permanent device, patients undergo an initial testing phase to estimate potential response to treatment. The first type of testing developed was percutaneous nerve evaluation (PNE). This procedure is done under local anesthesia, using a test needle to identify the appropriate sacral nerve(s). Once identified, a temporary wire lead is inserted through the test needle and left in place for 4 to 7 days. This lead is connected to an external stimulator, which can be carried by patients in their pocket, secured against the skin under surgical dressings, or worn in a belt. The results of this test phase are used to determine whether patients are appropriate candidates for the permanent implanted device. For example, for overactive bladder, if patients show a 50 percent or greater reduction in symptom frequency, they are deemed eligible for the permanent device.

The second type of testing is a 2-stage surgical procedure. In Stage 1, a quadripolartined lead is implanted (stage 1). The testing phase can last as long as several weeks, and if patients show a specified reduction in symptom frequency, they can proceed to Stage 2 of the surgery, which is permanent implantation of the neuromodulation device. The 2-stage surgical procedure has been used in various ways. These include its use instead of PNE, for patients who failed PNE, for patients with an inconclusive PNE, or for patients who had a successful PNE to further refine patient selection.

In one aspect, the duration of battery life of the EPG is at least four weeks for a tined lead at nominal impedance (e.g. about 1200 Ohms), an amplitude of about 4.2 mA, and a pulse width of about 210 us, or the duration of battery life can be at least seven days for a PNE lead. In some embodiments, the battery is rechargeable and can be recharged by coupling the battery with a standard 120 V wall outlet, and may optionally utilize the same power cables or adapter as used by other system components (e.g. clinician programmer). Typically, the EPG is current controlled. The EPG can be configured with a pulse width between 60-450 μs, a maximum stimulation rate between 2 and 130 Hz, a maximum amplitude between 0 and 12.5 mA, a stimulation waveform that is biphasic charge-balanced assymetric, minimum amplitude steps of about 0.05 mA, continuous or cycling operating modes, a set number of neurostimulation programs (e.g. two programs), ramping capability, and optional alert built into the EPG.

The permanent device is implanted under local or general anesthesia. An incision is made over the lower back and the electrical leads are placed in contact with the sacral nerve root(s). The wire leads are extended underneath the skin to a pocket incision where the pulse generator is inserted and connected to the wire leads. Following implantation, the physician programs the pulse generator to the optimal settings for that patient.

One example of a common process for treating bladder dysfunction is to employ a trial period of sacral neuromodulation with either a percutaneous lead or a fully implanted lead in patients that meet all of the following criteria: (1) a diagnosis of at least one of the following: urge incontinence; urgency-frequency syndrome; non-obstructive urinary retention; (2) there is documented failure or intolerance to at least two conventional therapies (e.g., behavioral training such as bladder training, prompted voiding, or pelvic muscle exercise training, pharmacologic treatment for at least a sufficient duration to fully assess its efficacy, and/or surgical corrective therapy); (3) the patient is an appropriate surgical candidate; and (4) incontinence is not related to a neurologic condition.

Permanent implantation of a sacral neuromodulation device may be considered medically necessary in patients who meet all of the following criteria: (1) all of the criteria (1) through (4) in the previous paragraph are met; and (2) trial stimulation period demonstrates at least 50% improvement in symptoms over a period of at least one week.

Other urinary/voiding applications of sacral nerve neuromodulation are considered investigational, including but not limited to treatment of stress incontinence or urge incontinence due to a neurologic condition, e.g., detrusor hyperreflexia, multiple sclerosis, spinal cord injury, or other types of chronic voiding dysfunction. (See policy description of sacral nerve neuromodulation/stimulation coverage provided by Blue Cross Blue Shield available online at: http://www.bcbsms.com/com/bcbsms/apps/PolicySearch/views/ViewPolicy. php?&noprint=yes&path=%2Fpolicy %2Femed %2F Sacral_Nerve_Stimulation.html)

In another conventional approach, a similar method is used in peripheral neurostimulation (PNS) treatment systems. Generally, candidates for peripheral neurostimulation are assessed to determine their suitability for undergoing the PNS procedure. Prior to the surgery, the patient will undergo pre-surgical testing that includes routine blood tests as well as neuropsychological evaluation. The PNS procedure itself is typically performed in two separate stages. Each stage takes about one hour, and the patient can go home the same day.

In this aspect, Stage 1 involves implanting of trial electrodes, via small needles, which are connected to an external pulse generator (EPG), typically worn on a belt of the patient. A number of stimulation programs are administered over the next few days. If this trial demonstrates a significant improvement in the patient's headache or facial pain, permanent implantation can take place. In Stage 2, a new set of electrodes, the width of angel-hair pasta, are implanted under the skin. These are connected to a smaller implantable pulse generator implanted under the skin in the chest, abdomen, or back.

Among the drawbacks associated with these conventional approaches, is the discomfort associated with wearing an EPG. The effectiveness of a trial period such as in PNE and Stage 1 trial periods are not always indicative of effective treatment with a permanent implanted system. In one aspect, since effectiveness of treatment in a trial period may rely, in part, on a patient's subjective experience, it is desirable if the discomfort and inconvenience of wearing an EPG by the patient can be minimized so that the patient can resume ordinary daily activities without constant awareness of the presence of the EPG and treatment system. This aspect can be of particular importance in treatment of overactive bladder and erectile dysfunction, where a patient's awareness of the device could interfere with the patient's experience of symptoms associated with these conditions.

In one aspect, the invention allows for improved assessment of efficacy during trial periods by providing a trial system having improved patient comfort so that patients can more easily recognize the benefits and effectiveness of treatment. In another aspect, the portions of the EPG delivering the therapy are substantially the same as the IPG in the permanent system such that the effects in permanent treatment should be more consistent with those seen in the trial system.

In certain embodiments, the invention provides an EPG patch worn on a skin of the patient so as to improve patient comfort. Optionally, the EPG used in Stage 1 may be smaller than the IPG used in the corresponding Stage 2 so that the EPG can easily be supported by and sealed against contamination by an adherent patch that covers the EPG. In one aspect, the EPG is a modified version of the implantable IPG used in Stage 2. The IPG may be modified by removal of one or more components, such as removal of a remote charging coil with a smaller battery and associated components. In addition, the EPG may use a thinner, lighter housing than the IPG, since the EPG is not required to last for many years, such as the IPG would be. The EPG therefore, may be configured to be disposable. These aspects allow the EPG to be supported within a patch adhered to the skin of the patient at a convenient and comfortable location.

FIG. 1 illustrates an example trial neurostimulation system 100 having an EPG patch 10. As shown, the neurostimulation system is adapted to stimulate a sacral nerve root. The neurostimulation system 100 includes an implantable pulse generator (IPG) implanted in a lower back region, from which a neurostimulation lead 20 extends through a foramen of the sacrum to electrodes (not shown) disposed near the sacral root. The neurostimulation lead 20 further includes an anchor 10 disposed on a dorsal side of the sacrum. It is appreciated, however, that the anchor may be disposed on a ventral side of the sacrum as well, or within the foramen itself. In one aspect, the EPG 40 is disposable and discarded after the trial is complete. Typically, the trial may last anywhere from 4 days to 8 weeks. Typically, an initial assessment may be obtained after 4-7 days and, if needed, effectiveness of treatment may be examined after a few weeks, typically about 2 weeks. In one aspect, the EPG 40 of the EPG patch 10 is of a substantially similar design as the IPG that would be implanted if the trial proves successful, however, one or more components may be removed to allow the EPG to be smaller in size, lower in mass, and/or differing materials are used since the device may be intended for one time use.

Figure 2A:
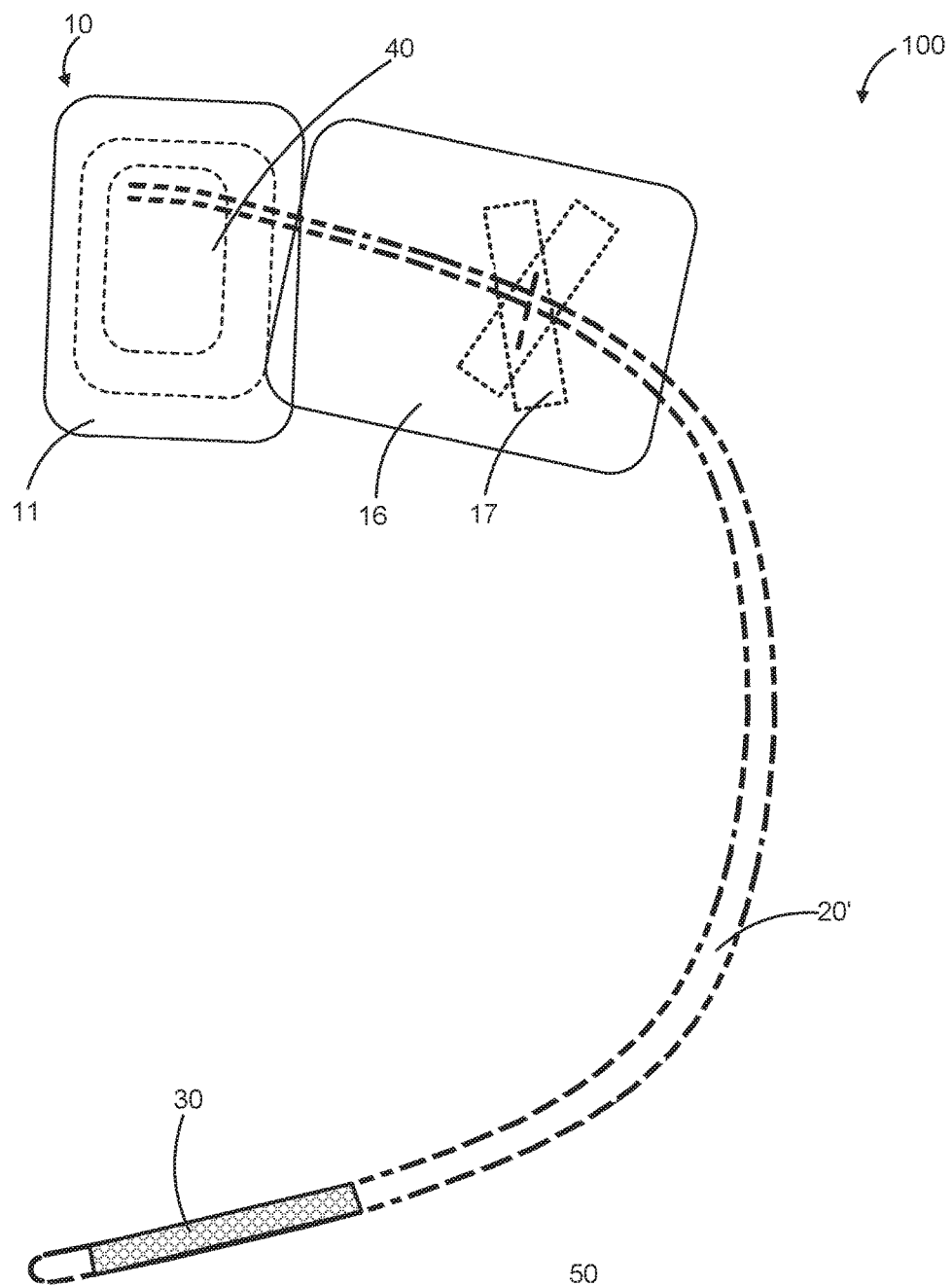
FIGS. 2A and 2B are example overviews of the neurostimulation system of FIG. 1.

FIG. 2A shows an embodiment of neurostimulation system 100, similar to that in FIG. 1, in more detail. As can be seen, the neurostimulation lead 20' includes a neurostimulation electrode 30 at a distal end configured for PNE use. The EPG 40 is supported within an adherent patch 11 when attached to a skin of the patient.

Figure 2B:
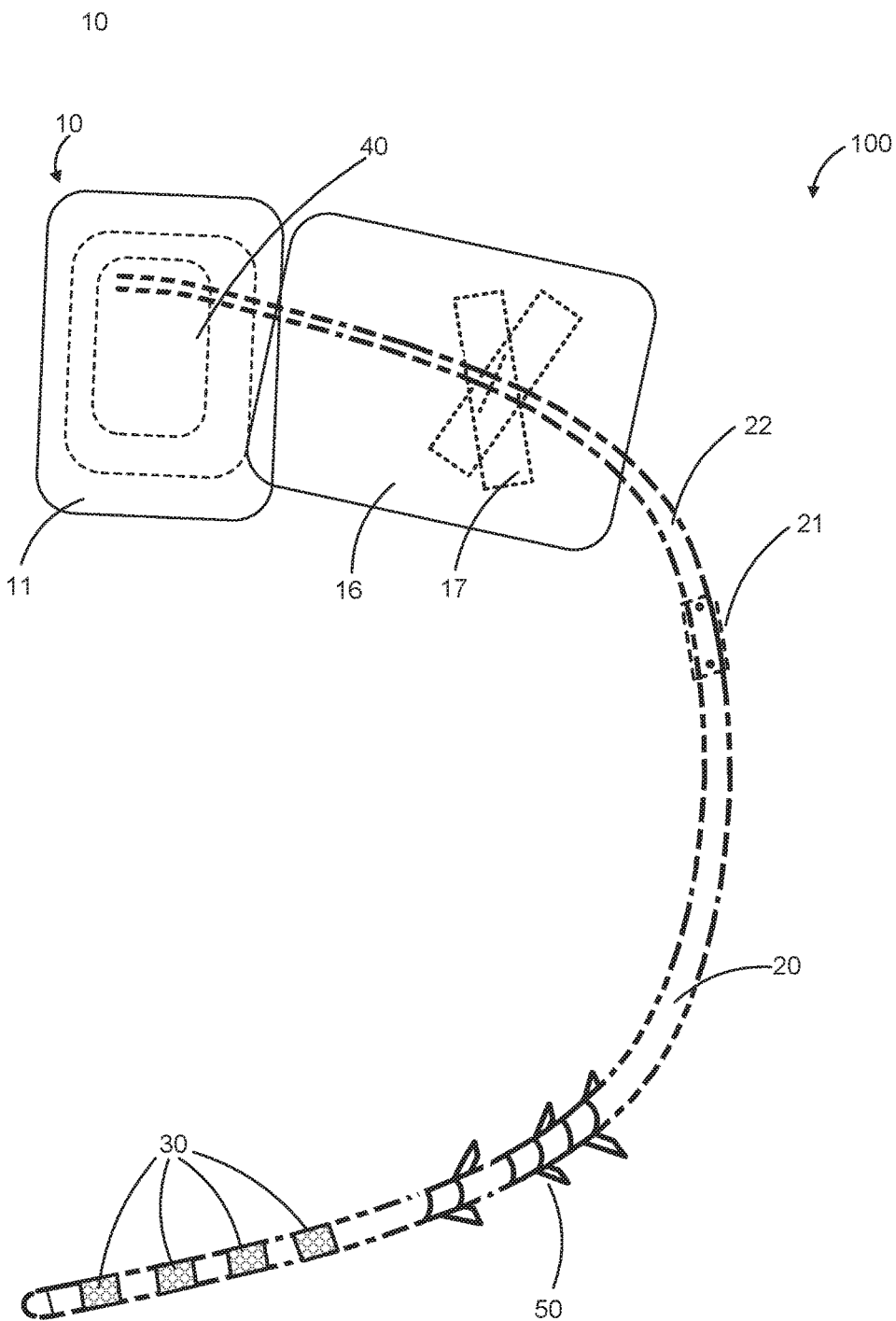

FIG. 2B illustrates an alternate embodiment of neurostimulation system 100, similar to that in FIG. 1, in more detail. Neurostimulation lead 20 is attached to EPG 40 via extension cable 22 and connector 21. As can be seen, the neurostimulation lead 20 includes a plurality of neurostimulation electrodes 30 at a distal end of the lead and an anchor 50 having a plurality of tines disposed just proximal of the electrodes 30. Typically, the anchor is disposed near and proximal of the plurality of electrodes so as to provide anchoring of the lead relatively close to the electrodes. The EPG 40 is supported within an adherent patch 11 when attached to a skin of the patient.

In one aspect, additional adherent patches 16 may be used to cover and seal the percutaneous incision in the skin of the patient through which the percutaneous portion of the neurostimulation lead is inserted. The lead may be secured at the percutaneous incision with surgical tape 17 and further secured and sealed with an adherent patch covering the lead and percutaneous incision. In this manner, the percutaneous incision can be sealed and protected from contamination or infection and its position maintained by the additional adherent patches 16. This configuration reduces the likelihood of infection and prevents movement of the lead, both internal and external, such that the patient's awareness of the patch and lead is minimized, thereby allowing the patient to resume relatively normal daily activities.

In another aspect, since the EPG patch may be worn in a different location, such as on the abdomen, than the IPG would be implanted, to allow the IPG to use the same fully implanted neurostimulation lead 20, the system may use a lead extension 22 coupled with the lead 20 by an implanted connector 21. The lead extension 22 may optionally be hardwired into the EPG so as to eliminate potential disconnection and allow the connection to be sealed or encapsulated within the adherent patch so as to be water resistant or water proof. This allows the patient to perform routine daily activities, such as showering without removing the device. The length of lead 20 may be a suitable length for the permanently implanted system, while the length of extension 22 allows the lead to EPG patch to be positioned in a location that provide improved comfort and minimized interference with daily activities.

Figure 3A:
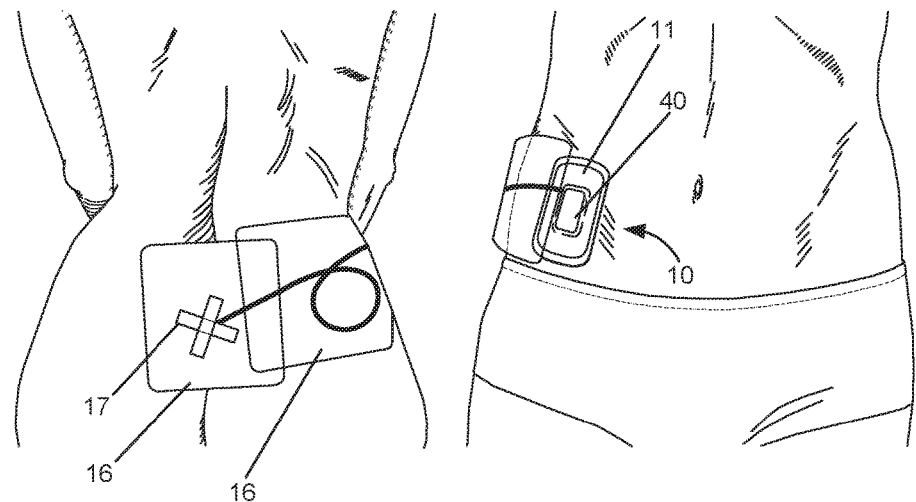
FIG. 3A is an alternative configuration of a trial neurostimulation system, in accordance with some embodiments.

FIG. 3A illustrates an alternate configuration in which the lead is sufficiently long to allow the EPG patch 10 to be placed to allow the patient more mobility and freedom to resume daily activities that does not interfere with sitting or sleeping. Excess lead can be secured by an additional adherent patch 16, as shown by the center patch in FIG. 3A. In one aspect, the lead is hardwired to the EPG, while in another the lead is removable connected to the EPG through a port or aperture in the top surface of the flexible patch 11. In one aspect, the EPG patch and extension cable are disposable such that the implanted lead can be disconnected and used in a permanently implanted system without removing the distal end of the lead from the target location. In another aspect, the entire trial system can be disposable and replaced with a permanent lead and IPG.

In one aspect, the EPG unit may be wirelessly controlled by a patient remote in a similar or identical manner as the IPG of a permanently implanted system would be. The physician may alter treatment provided by the EPG through use of a portable clinician unit and the treatments delivered are recorded on a memory of the device for use in determining a treatment suitable for use in a permanently implanted system.

Figure 3B:
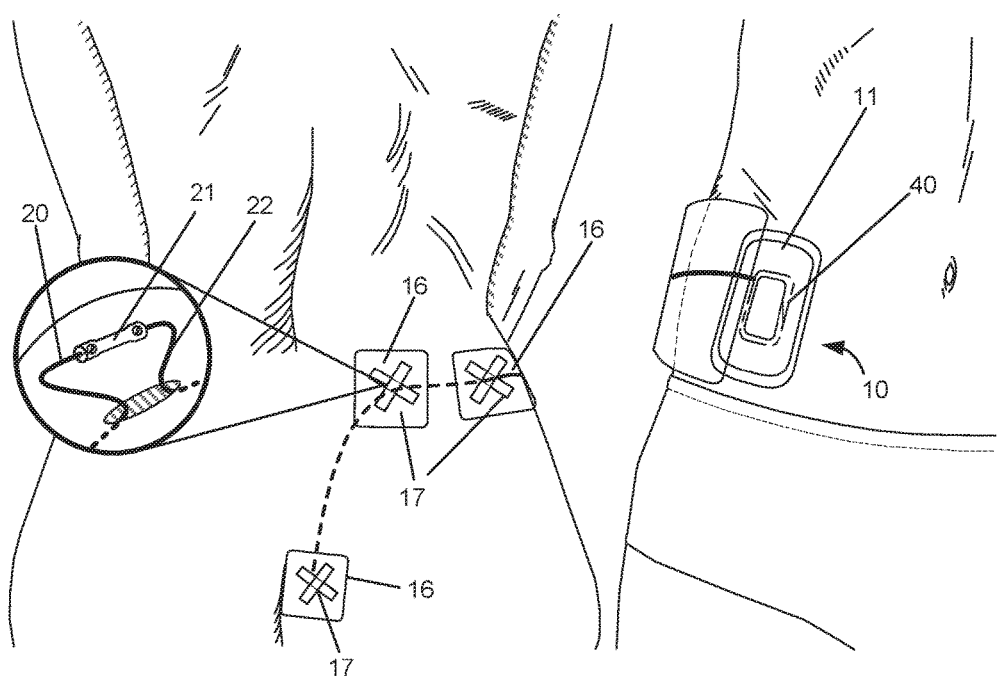
FIG. 3B is yet another alternative configuration of a trial neurostimulation system, in accordance with some embodiments.

FIG. 3B illustrates an alternate configuration in which the lead 20 is connected to a lead extension 21 through a connector 21. This allows for the implanted lead to be used for both the trial and permanent system. This also allows the lead 20 of a length suitable for implantation in a permanent system to be used. Three access locations are shown: two percutaneous puncture sites, one for the lead implantation over the sacral area, and one for the extension exit site, while in between the puncture locations an incision (>1 cm) is made for the site of the connection of the lead 20 and the extension cable 22.

This approach minimized movement of the implanted lead 20 during conversion of the trial system to a permanently implanted system. During conversion, the lead extension 22 can be removed along with the connector 21 and the implanted lead 20 attached to an IPG that is placed permanently implanted in a location at or near the site of the first percutaneous incision. In one aspect, the connector 21 may include a connector similar in design to the connector on the IPG. This allows the proximal end of the lead 20 to be coupled to the lead extension 22 through the connector 21 and easily detached and coupled to the IPG during conversion to a permanently implanted system.

FIG. 3C illustrates a detailed view of an EPG patch adhered to the skin of the patient, an additional adherent patch 16 disposed over the percutaneous incision through the lead extends into the patient and another additional patch 16 covering a loop of excess lead, the patch overlapping the first additional patch and the edge of the EPG patch 10. This configuration is advantageous as it substantially covers and seals the EPG and the lead from contamination and prevents accidental disconnection or migration of the lead by the patient, and streamlines the external portions of the system so as to improve patient comfort and allow a patient's subjective experience to more closely match what the patient would experience in a permanently implanted system.

FIGS. 4A-4C illustrates an overhead view and side views of an embodiment of EPG 40 that is smaller than a subsequently used IPG. Such an EPG can be situated within an EPG adherent patch affixation device 10, or in any other affixation device described herein. In one aspect, the EPG is smaller than the IPG in the corresponding fully implantable permanent system. In certain embodiments, the outside width (w2) of the adherent patch 11 is between 2 and 5 inches, preferably about 2.5 inches, while the outside length (l2) of the patch 11 is between 3 and 6 inches, preferably about 4 inches; the width of the EPG (w1) is between 0.5 and 2 inches, preferably about 1 inch, while the length (l1) is between 1 and 3 inches, preferably about 2 inches; and the thickness (t) of the entire EPG patch 10 is less than 1 inches, preferably 0.8 inches or less. This design is considerably smaller than EPGs in conventional systems and thus interferes less with the daily activities of the patient during the trial period. The above described dimensions can be applicable to any of the embodiments described herein. Although in this embodiment, adherent patch 11 encapsulates the EPG within an interior cavity, it is appreciated that the EPG could be coupled with an adherent patch in any number of ways, including use of various coupling features. In some embodiments, the EPG is supported within a pouch of a belt or covered by an adhesive patch or surgical tape. In some embodiments, such as those described below, such coupling features can be configured to allow for ready removal of the EPG from the affixation device.

The underside of the adherent patch affixation device 11 is covered with a skin-compatible adhesive. The adhesive surface may be configured with any adhesive or adherent material suitable for continuous adhesion to a patient for the direction of the trial period. For example, a breathable strip having skin-compatible adhesive would allow the patch 12 to remain attached to the patient continuously for over a week, typically two weeks to four weeks, or even longer.

These aspects can be included on any of the affixation devices described herein that couple to the patient by means of an adhesive surface.

Figure 5:
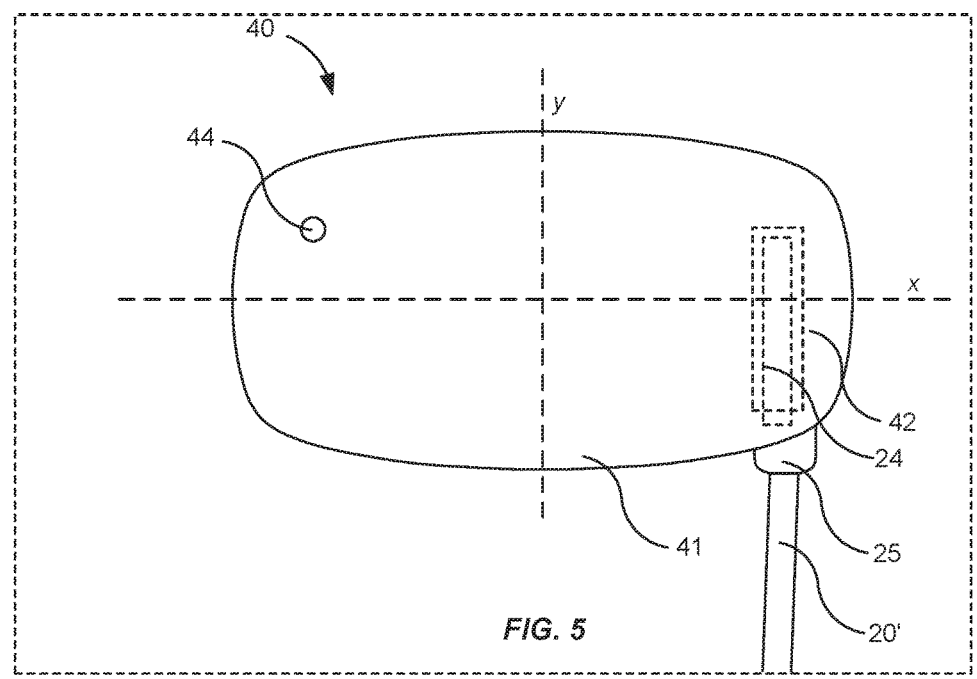
FIG. 5 illustrates an EPG and an associated schematic in accordance with some embodiments.

FIG. 5 illustrates an example EPG 40 for use in a neurostimulation trial in accordance with various aspects of the invention. EPG 40 includes a substantially rigid outer shell or housing 41, in which is encased a stimulation pulse generator, a battery and associated circuitry. EPG 40 also includes a connector receptacle 42 accessed through an opening or port in the outer housing 41 and adapted to electrically connect with a proximal lead connector 24 of a neurostimulation lead 20'. Although EPG 40 is shown connected with neurostimulation lead 20', lead 20, cables 22,26, and 27 may also be connected to EPG 40. Connector receptacle 42 includes multiple electrical contacts (e.g. six contact pins, eight-contacts pins), all or some of which can be connected to corresponding contacts points on a connector coupled thereto, depending on the type of connector. Connector receptacle 42 could be configured according to varying types of connector standards beyond that shown, for example, a USB or lightning cable connector. Lead connector 24 can include a proximal plug or boot 25 that sealingly engages the port when lead connector 24 is matingly connected within connector receptacle 42 to further secure the mated connectors and seal the port from intrusion of water, humidity or debris. Boot 25 can be formed of a pliable material, such as an elastomeric polymer material, that is fitting received within the port so as to provide ingress protection. In some embodiments, this configuration provides an ingress protection rating (IPR) is provided at IP24 or better. In this embodiment, connector receptacle 42 includes multiple electrical contacts, each operatively coupled with the stimulation pulse generator, so that the EPG can deliver neurostimulation pulses to multiple neurostimulation electrodes of the lead when coupled to the connector receptacle 42.

In one aspect, EPG 40 is configured with a multi-purpose connector receptacle 24. For example, connector receptacle 42 can be coupled with either a neurostimulation lead 20' as described above, or can be coupled with a power connector of a charging cord to allow recharging of an internal battery of EPG 40. Such a configuration is advantageous as it allows the EPG housing 41 to be designed with a single opening or access port, which further reduces the potential exposure of internal components to water and debris, since the port is sealingly occupied by the lead connector during delivery of therapy during the trial period. In contrast, a device having a separate charging port would likely either remain open or may require use of a removable plug or cover to seal the additional port. EPG 40 can further be configured with multiple operating modes, each mode suited for a different purpose for which connector receptacle 42 can be used. Such modes can include a therapy operating mode in which the stimulation pulse generator of EPG 40 delivers stimulation pulses to the neurostimulation lead connected to connector receptacle 24, and a charging mode in which a rechargeable battery within EPG 40 receives power. In some embodiments, EPG 40 includes only two operating modes, the therapy mode and charging mode. In other embodiments, EPG 40 can include various other operating modes, including but not limited to, various testing modes, a dual lead mode, a bipolar mode, and a monopolar mode. Such modes can correspond to differing connectors of a specialized cable set, such as any of those shown in FIG. 12B-12F.

EPG 40 can further include an indicator 44, such as an LED, that indicates a status of the EPG 40, which can include an ON/OFF state, a hibernation state, a mode, or a charge state (e.g. "charging needed," "low", "fully charged", "charging"). In some embodiments, indicator 44 is configured with differing colored LEDs that indicate differing states by displaying different colors. For example, a red light output can indicate "charging needed", an orange light output can indicate "low" charge, and a green light output can indicate a "fully charged" status). Differing modes or status of EPG 40 could also be indicated by use of multiple lights or flashing or blinking patterns (e.g., flashing green indicates the EPG is "charging").

In another aspect, EPG 40 is designed as a substantially planar polygonal prism having parallel major surfaces that are positioned flat against the patient's body when affixed to the patient during the trial period, such as the rectangular prism shown in FIG. 5. In this embodiment, EPG 40 is a substantially rectangular shape with rounded corners and curved edges, the x-axis extending along a lengthwise direction of the rectangle, they-axis extending along a widthwise direction of the rectangle and the z-axis (not shown) extending along a thickness direction. As shown, the corners and edges are rounded or chamfered for improved patient comfort when worn against the patient's abdomen or on the patient's belt. While a substantially rectangular shape with rounded edges is depicted here, it is appreciated that EPG 40 can be formed in various other shapes (e.g. circular, triangular, square, symmetrical or non-symmetrical shapes), and still be suited for use with affixation devices according to the principles described herein.

Figure 6:
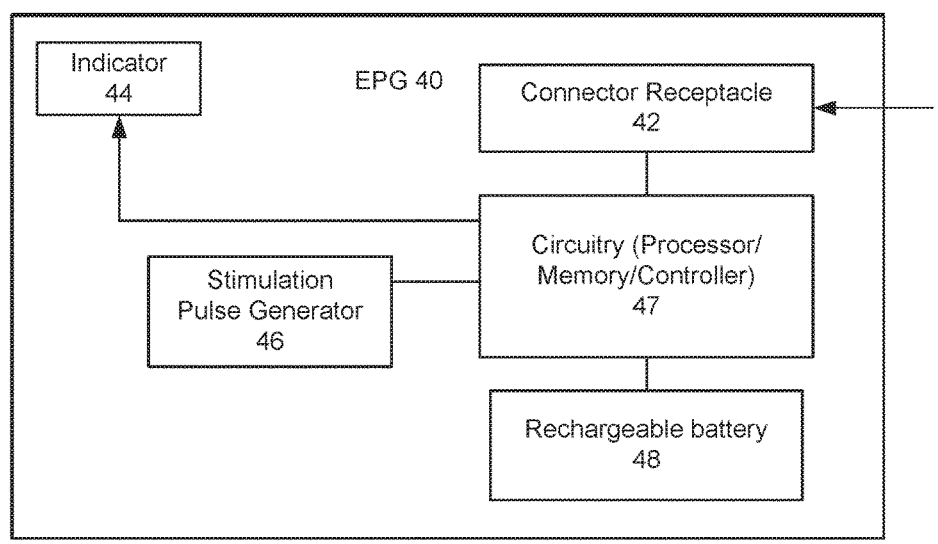
FIG. 6 shows a schematic of an EPG in accordance with some embodiments.

FIG. 6 shows a schematic of the example EPG 40 having a multi-purpose connector receptacle 42. EPG 40 includes the stimulation pulse generator 46 and rechargeable battery 48 each coupled to connector receptacle 42 via associated circuitry 47 that controls delivery of power to and from the rechargeable battery 48 and the stimulation pulse generator 46 and connector receptacle 42. Circuitry 47 can include one or more processors, controllers and a recordable memory having programmable instructions recorded thereon to effect control of the stimulation pulse generation, rechargeable battery discharge and charging, and indicator 44. In some embodiments, memory includes pre-programmable instructions configured to effect multiple different operating modes, for example the therapy mode and charging mode. In the therapy mode, circuitry 47 uses the rechargeable battery 48 to power the stimulation pulse generator 46, which produces stimulation pulses that are delivered to a connected neurostimulation lead via the connector receptacle 42. In the charging mode, circuitry 47 controls delivery of power delivered via the connector receptacle 42 to rechargeable battery 48. In some embodiments, circuitry 47 includes a controller that switches between differing modes, which can be effected upon connection of a certain connector types into connector receptacle 42. For example, in some embodiments, EPG 40 can include a detector that can detects a certain type of connector (e.g. lead connector, charging connector). In other embodiments, a connector type can be determined by measurement or detection of electrical characteristics of the connection. For example, a charging connection may require electrically connectivity with only a certain number of electrical contacts (e.g. one, two, etc.) and a ground, while a neurostimulation lead may connect with all of the designated electrical contacts without any grounding required. In some embodiments, the mode can be set be manually or wirelessly set by a user as needed.

In some embodiments, EPG 40 is configured to suspend generation of stimulation pulses upon disconnection of any connector within the connector receptacle. Configuring the EPG with a detachable cable improves safety of the device by preventing stimulation pulse output through the connector receptacle if the neurostimulation lead or associated cable should become accidentally caught and dislodged or intentionally removed by the user. This aspect may be effected by detection of a loss of connectivity or any other means of determining that the connector has been removed. In other embodiments, the EPG does not include any built-in cable, but can include one or more connectors that allow the patient to readily attach and detach cables as needed.

In another aspect, trial neurostimulation system 100 includes an affixation device that secures EPG 40 to the patient while connected to a neurostimulation lead implanted at a target tissue within the patient. Typically, the affixation device is configured to secure the EPG on a mid-portion (e.g. lower back region) or hip of the patient, either through an adherent patch applied directly to a skin of the patient or a clip device that can be releasably attached to a garment of the patient. Various examples of differing types of affixation devices are described herein.

In one aspect, such an affixation device can be configured to allow the user to readily remove the EPG device. Such a configuration may be useful for certain activities, such as bathing or sleeping, and can improve patient compliance during the trial period. When patients are subjected to a trial therapy in which an EPG is fixedly secured to the skin with an adhesive patch, some patients may find the presence of the EPG to be too invasive or uncomfortable to continue with the trial, which prevents a determination of the suitability of neurostimulation therapy and greatly reduces the likelihood that the patient will proceed with a fully implanted system, even though the fully implanted system would not present the same discomfort. Therefore, providing an affixation device that secures the EPG to the patient but still allows for ready removal of the EPG (assuming a removable, detachable EPG) can further improve the success rate of the trial period and improve determinations of whether a patient is a candidate for a permanently implanted neurostimulation system.

Figure 7A:
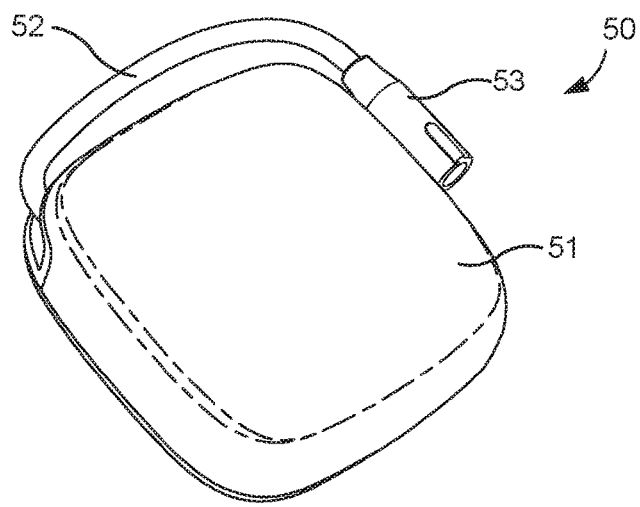
FIGS. 7A-7B illustrate an alternative EPG in accordance with some embodiments.
Figure 7B:
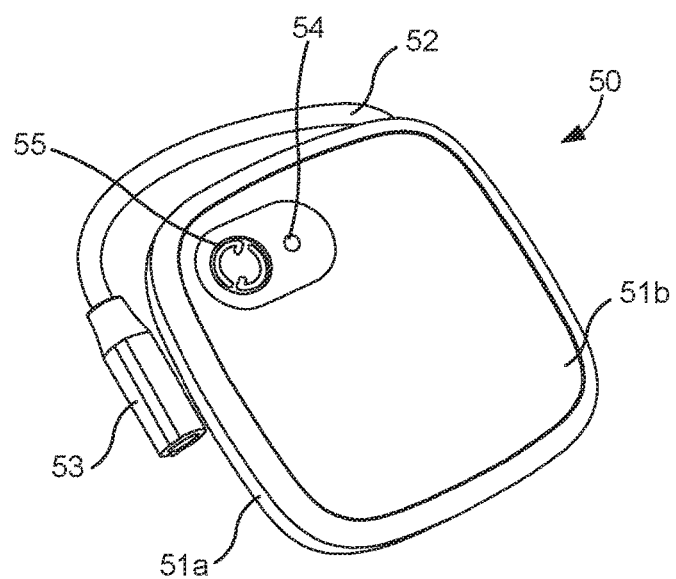

FIGS. 7A-7B illustrate an alternative EPG 50 that includes a housing 51 from which a short cable connector 52 extends to a lead connector 53. In this embodiment, lead connector 53 is a multi-pin connector suitable for electrically connecting to a neurostimulation lead having multiple electrodes through an intermediate adapter or lead extension cable (see FIG. 13). Typically, cable connector 52 is relatively short, for example a length between 1 and 12 inches, preferably 3 and 6 inches. In this embodiment, the multi-pin connector is a 4-pin connector suitable for connecting to a neurostimulation lead having four electrodes, however, it is appreciated that lead connector could include differing numbers of pins so as to be suitable for connection with neurostimulation leads having greater or fewer neurostimulation electrodes. In other embodiments, the lead connector can be configured with a receptacle 42 for connecting with a proximal lead connector of a neurostimulation lead, such as described previously in other embodiments. The EPG can be used with a tined lead trial or a temporary lead (PNE lead) trial. Configuring the connection to the lead external of the housing allows the EPG to be even smaller and lighter than those with the connection integrated within the device. Such a configuration also allows for some movement for adjustment or handling of the EPG while minimizing movement of the proximal lead connector, which can be secured by tape to the patient's body just proximal of the connector.

In some embodiments, the short cable connector 52 or "pigtail connector" is integrated with the EPG such that the electrical connections between the cable and the internal electronics of the EPG are permanently attached and sealed. This allows the EPG to further withstand intrusion of fluids and moisture during the trial stimulation period.

Depending on the selection of cables desired for use, the EPG may be used with a PNE lead (which may have one or more than one electrode and conductor), or a permanent lead. In addition, the EPG may be used for bilateral stimulation (the use of two leads, one for each for a patient's left and right sides) when a bilateral connector cable is used between the EPG and leads.

In some embodiments, the EPG includes a non-rechargeable single-use power source (e.g. battery) having sufficient power for operation of the EPG for at least the duration of the trial period (e.g. days, weeks, months). In such embodiments, the power source can be integrated and non-removable or non-replaceable by the patient.

As can be seen in FIG. 7B, EPG housing 51 can be defined as two interfacing shells, top shell 51a defining the outer major surface and a majority of the side surfaces and bottom shell 52b defining an underside surface. In this embodiment, EPG has a substantially rectangular (e.g. square) prism with rounded edges. The top major surface can be shaped with a slightly convex contour, while the underside includes a substantially flattened surface for placement against the patient. Typically, the interfacing shells 51a, 52b are formed of a rigid or semi-rigid material, such as hardened polymer, so as to protect and seal the electronics within.

Figure 7C:
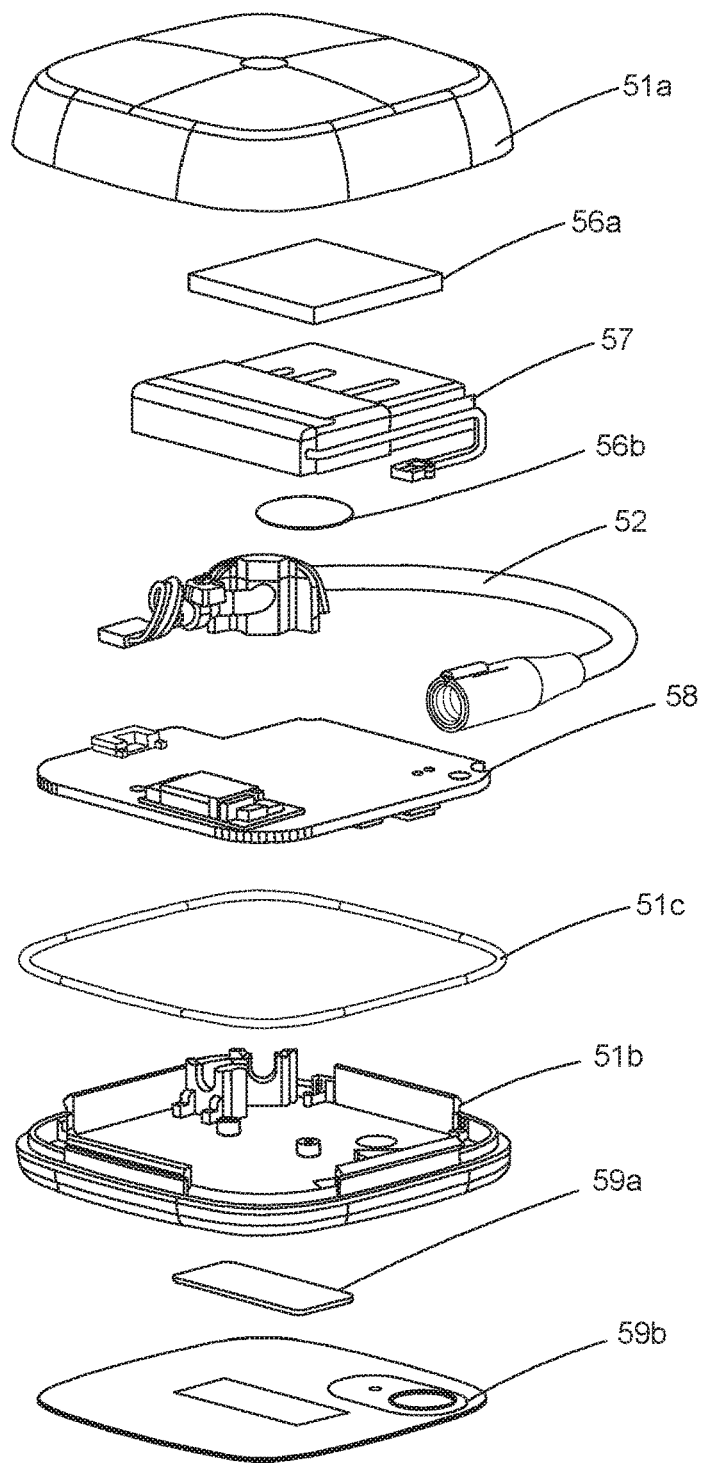
FIG. 7C shows an exploded view of the EPG in FIGS. 7A-7B.

As shown in the exploded view of FIG. 7C, EPG 50 includes top housing shell 51a, compressible foam sheet 56a, battery 57, double-sided adhesive disc 56b, short electrical connector cable 52, printed circuit board 58, O-ring 51c for sealing top housing shell 51a with bottom shell 51b, and serial number label 59a and outer label 59b, which are affixed to the underside of bottom shell 51b. It is appreciated that this arrangement of elements is exemplary and various other arrangements are within the scope of the invention.

In some embodiments, the EPG includes one or more user interface features. Such user interface features can include any of a button, switch, light, touch screen, or an audio or haptic feature. In the embodiment shown in FIGS. 7A-7B, EPG 50 includes a button 55 and an LED indicator 54. Button 55 is configured to turn EPG 50 on from an off or hibernation state. When turned on, EPG can communicate with an external device, such as a clinician programmer to receive programming instructions, and can deliver stimulation to a connected neurostimulation lead while in an operating state. While button 55 can be used by the patient to turn EPG 50 on, it is appreciated that this functionality can be concurrent with any other functionality described herein. For example, EPG 50 can be further configured to be turned on from an off or hibernation state by use of a patient remote or can be configured to suspend delivery of stimulation upon detachment of the neurostimulation lead. It is appreciated that while a button is described in this embodiment, any actuatable user interface feature could be used (e.g. switch, toggle, touch sensor) that is typically actuatable between at least two states.

In this embodiment, EPG 50 is configured such that pressing button 55 turns on a communication function of the EPG. Once actuated, the EPG has a pre-determined period of time (e.g. 60 seconds, 90 seconds) to wirelessly connect to an external programmer (e.g. Clinican Programmer). If the EPG connects to the clinician programmer, the EPG stays on to facilitate programming and operating to deliver of stimulation per programming instructions. If connection is not successful, the EPG automatically turns of. If button 50 is pressed when EPG is on, nothing happens and the communication or operating remains unchanged. If a patient desires to turn off stimulation, the patient remote could be used or alternatively, detachment of the neurostimulation lead could also suspend stimulation. Since subsequent pressing of button 55 during operation does not turn the EPG to the off or hibernation state, the button can be positioned on an underside of the EPG that is placed against the patient when worn during the trial stimulation period, although it is appreciated that the button could be disposed anywhere on the housing of the EPG. Thus, in this embodiment, the functionality of button 55 facilitates initial programming during set-up of the trial period or for reprogramming, but does not require interaction by the patient during the trial period. Typically, control or adjustment of stimulation by the patient would be performed by use of the patient remote. In some embodiments, the EPG is provided in a hibernation mode and communication can be initiated by actuation of a button on the EPG to facilitate programming with the CP. In some embodiments, when the patient remote is used to turn stimulation off, the EPG returns to the hibernation state and only the CP can fully turn the EPG to an off-state.

In this embodiment, EPG 50 further includes a LED indicator 54 that indicates a status of the EPG. The status can include a status of communication between the EPG and a programmer device, a battery status, an error status, or any combination thereof. LED indicator 54 can be configured with differing colors or blinking patterns to indicate differing status. For example, the EPG can be configured such that a flashing green light indicates communication is on; a solid green light indicates EPG is in operating mode and the battery is good; a solid orange or yellow indicates battery is at an acceptable charge; a flashing orange or yellow indicates the battery is low; and a red light indicates an error state. Since the information conveyed by the EPG may be more suited for use by the clinician, LED indicator 54 can be situated on an underside of the EPG placed against the patient when worn during the trial period, although it is appreciated that the LED could be disposed anywhere on the housing of the EPG.

Figure 8A:
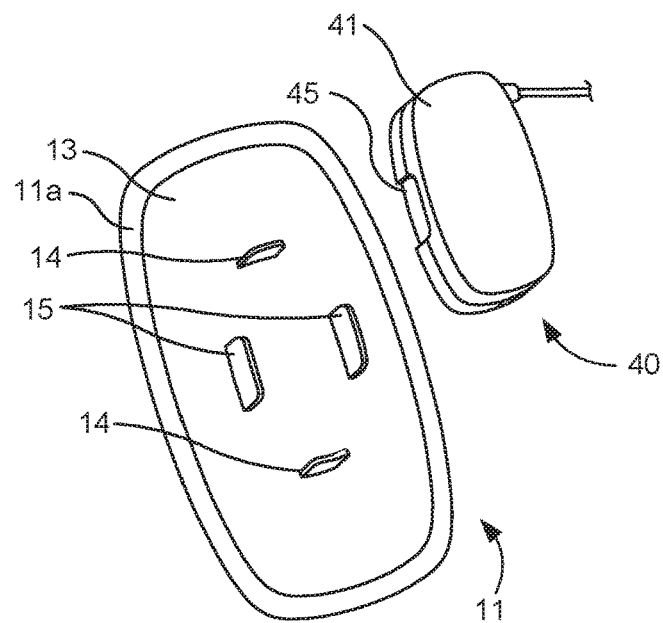
FIGS. 8A-8B illustrate an EPG and affixation device for use in a trial neurostimulation system in accordance with some embodiments.
Figure 8B:
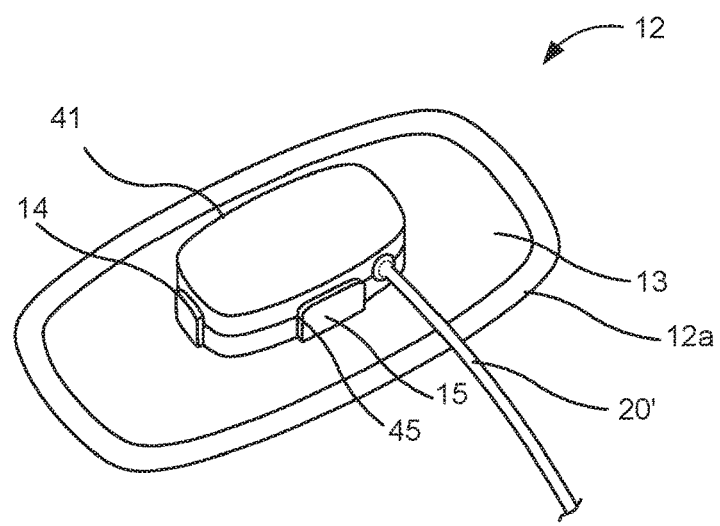
Figure 9A:
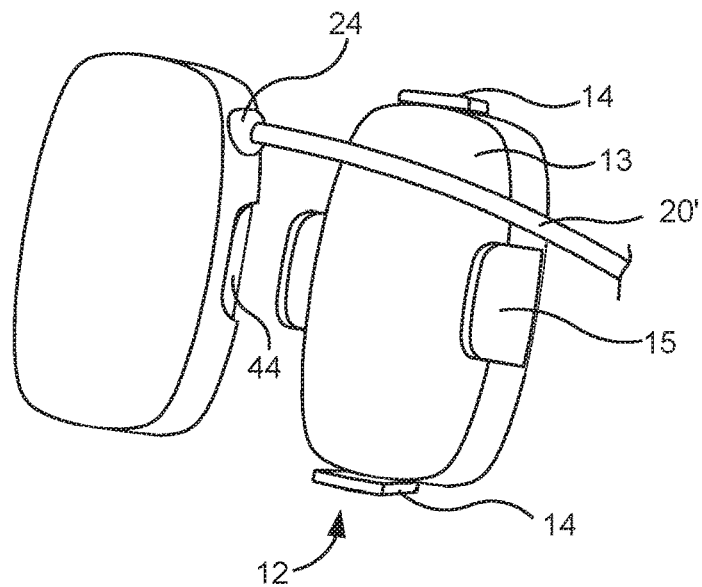
FIGS. 9A-9B illustrate an EPG and affixation device for use in a trial neurostimulation system in accordance with some embodiments.
Figure 9B:
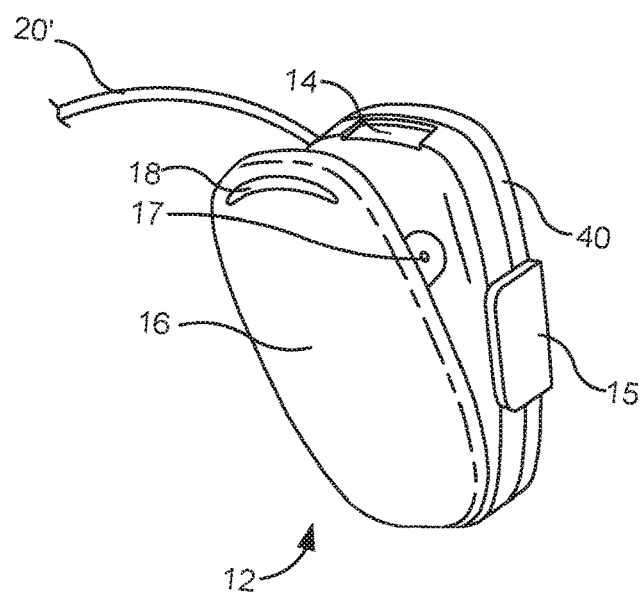

FIGS. 8A-8B and 9A-9B illustrate examples of affixation devices that secure the EPG to the patient while still allowing for ready removal. FIGS. 8A-8B illustrate an adherent patch affixation device 11 and FIGS. 9A-9B illustrate an adjustable clip affixation device 12. Each of these figures shows lead 20' by way of example, however, any lead capable of connecting to the EPG may be used, for example lead 20, 22, 26, or 27 may also be used.

FIG. 8A illustrates adherent patch affixation device 11 before mounting of EPG 40 thereto. Adherent patch affixation device 11 includes a support substrate 13 that includes a patient coupling portion on a first side and an EPG mounting portion on a second, opposite side. Typically, the mounting portion is formed of a non-electrically conductive material, such as an insulative polymer material such that the affixation device is without any separate electrodes or electrically conductive path for delivering stimulation directly to the skin of the patient. In this embodiment, the patient coupling portion includes an adhesive patch 11a disposed along a major surface of the first side of the substrate. Adhesive patch 11a typically includes a flexible breathable material having a pressure sensitive adhesive suitable for securing to a skin of the patient for an extended duration of time, for example, for part or all of the trial period. While the adhesive patch 11a may be flexible and breathable for patient comfort, support substrate 13 is typically substantially rigid or semi-rigid so as to support one or more EPG mounting features and maintain the EPG mounted thereto.

In this embodiment, the EPG mounting portion includes multiple outwardly extending tabs that engage an outer housing of the EPG along an outer perimeter, typically at least one tab on each major side of the EPG or distributed about the perimeter of the EPG housing.

As shown in FIGS. 8A-8B, the multiple tabs can include two pairs of tabs. A first pair of tabs 14 are adapted to engage opposite sides of EPG 40 along the widthwise direction, while a second pair of tabs 15 engage opposite sides of EPG 40 along the lengthwise direction. In this embodiment, the second pair of tabs are resiliently deflectable to outwardly deflect upon pressing EPG 40 in between tabs 15 so that tabs 15 retain EPG 40 therebetween. EPG 40 can further include corresponding coupling features that fittingly engage each of the pairs of tabs 14, 15. For example, EPG 40 can include recessed notches (not visible) that fittingly receive the first pair of tabs 14. When fitted within corresponding recessed, the first pair of tabs 14 can constrain movement of EGP 40 in both x and y directions. EPG 40 can further include retention features that engage corresponding retention features of the mounting portion of the affixation device. For example, the second pair of tabs 15 can be defined with an inwardly curved, contoured or stepped-in portion that fits within a correspondingly shaped retention recess 45 within the lengthwise sides of EPG 40. When the second pair of retention tabs 15 are resiliently received within retention features 45, the second pair of tabs further constrains movement of EPG 40 in a z-direction, as well as the x and y-directions. Thus, in combination, the first and second pair of tabs secure and support EPG 40 within the affixation device in a particular orientation so that the proximal lead connector 24 can be securely maintained within lead connector receptacle 42.

In another aspect, the multiple tabs can be dimensioned so that a majority of an outer perimeter of EPG 40 remains exposed so that a patient can readily grasp outer edges of EPG 40 and remove from the affixation device as needed. By leaving a majority of the perimeter exposed, this configuration allows the patient to grasp the EPG for ready release even when the EPG is affixed in a lower back region, where the patient cannot readily view the device during detachment. In some embodiments, the multiple tabs are dimensioned so that ¾ or more of the perimeter of EPG 40 remains exposed. In other embodiments, the multiple tabs are dimensioned so that ⅘ or more, or even 9/10 or more of the outer perimeter is exposed, so as to further facilitate ready grasping by the patient to facilitate ready removal. In some embodiments where EPG 40 is substantially rectangular in shape, such as in the embodiment of FIG. 8A, the multiple tabs are configured to engage each side of EPG 40 at or near a mid-portion. This configuration allows for improved support and retention of EPG 40 while allowing at least two diagonally opposed corners, typically all four corners, to remain exposed. This arrangement allows the patient to effect release by grasping the edges and/or corners of EPG 40 and twisting along one or more axis (x, y or z) so as to release the second pair of retaining tabs 15 from corresponding retention recesses 45 for ready removal of EPG 40. The patient can then detach lead connector 24 from connector receptacle 42 and charge or store EPG 40 as needed.

FIG. 9A illustrates a spring-clip affixation device 12 for releasably securing EPG 40 to the patient. Affixation device 12 includes a substantially rigid or semi-rigid support substrate 13 having a patient coupling portion (e.g. spring-clip) on one side and an EPG mounting portion with one or more coupling features on an opposite side. Similar to the embodiment in FIG. 8A, the EPG mounting portion includes two pairs of tabs, a first pair of tabs 14 and a second pair of tabs 15 with retention features, each pair of tabs adapted to fittingly engage with corresponding features in the outer housing 41 of EPG 40 so as to securely mount EPG 40 to the substrate while allowing the patient to grasp and readily release EPG 40 from the affixation device 12, as described above with respect to the embodiment of FIG. 8A. In this embodiment, the patient coupling feature includes clip 16 that extends along the backside of substrate 13 and is separable from and biased towards substrate 13 so that a piece of the patient's garment or belt can be inserted therebetween. In this embodiment, clip 16 is pivotally coupled to substrate by a pivotal coupling 17 that is loaded with a spring to bias clip 16 towards the substrate. Clip 16 can further include a grasping feature 18 on an outer facing surface near a base of clip 16 so that the patient can readily grasp clip 16 and remove the clip by pressingly engaging the base and separate clip 16 from substrate 14 to release the garment or belt from the clip. Alternatively, the patient could grasp and release EPG 40 from the mounting portion of the clip affixation device 12, as described above, while leaving the clip 16 attached to the belt or garment. Typically, substrate 13 and clip 16 are formed of a substantially rigid or semi-rigid formable material, such as plastic. Clip 16 can be further configured to fit into a specialized belt.

Figure 10:
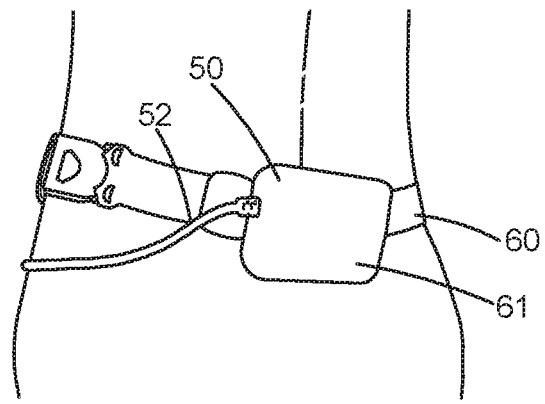
FIG. 10 illustrates an example EPG supported in a pouch of a belt for use in a trial neurostimulation system in accordance with some embodiments.
Figure 11:
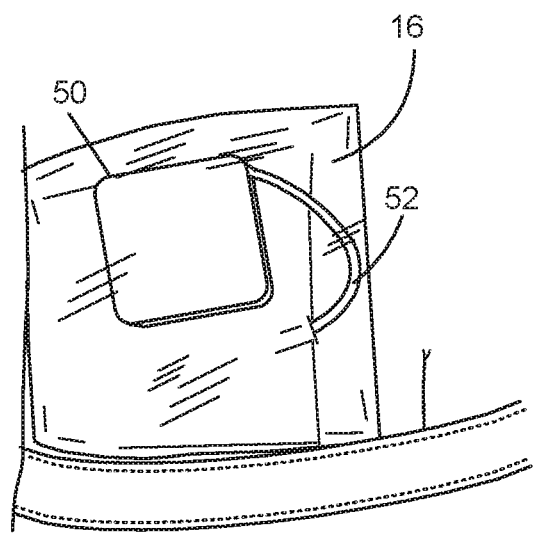
FIG. 11 illustrates an example EPG covered by an adhesive patch or tape for use in a trial neurostimulation system in accordance with some embodiments.

In another aspect, any of the EPG devices described herein can be supported by an adherent patch, as described previously, or can be supported by various affixation devices, such as any of those described. For example, as shown in FIG. 10, EPG 50 can be supported in a pouch 61 of an adjustable belt 60 worn by the patient. Pouch 61 can be formed of a flexible compliant or non-compliant material to improve patient comfort during the trial period. Alternatively, as shown in FIG. 11, EPG 50 can be supported by covering the EPG with an adhesive patch 16 or surgical tape. Since, in some embodiments, the EPG does not require patient interaction with the device during the trial period, the EPG can be completely covered during the trial period. Any adjustment or suspension of EPG operation by the patient during the trial period can be made by the patient remote.

While the above described embodiments depict examples of patient coupling features and EPG mounting features, it is appreciated that such features could be modified to accommodate EPGs of varying sizes and shapes and still retain the use and advantages of such features as described herein. For example, affixation devices having an EPG mounting portion could include only the two retention tabs or could include four retention tabs to provide varying levels of support and retention as needed for a particular EPG configuration. In other embodiments, the multiple tabs could dimensioned and arranged to engage the EPG at various other locations depending on the size and shape of the EPG device.

Figure 12:
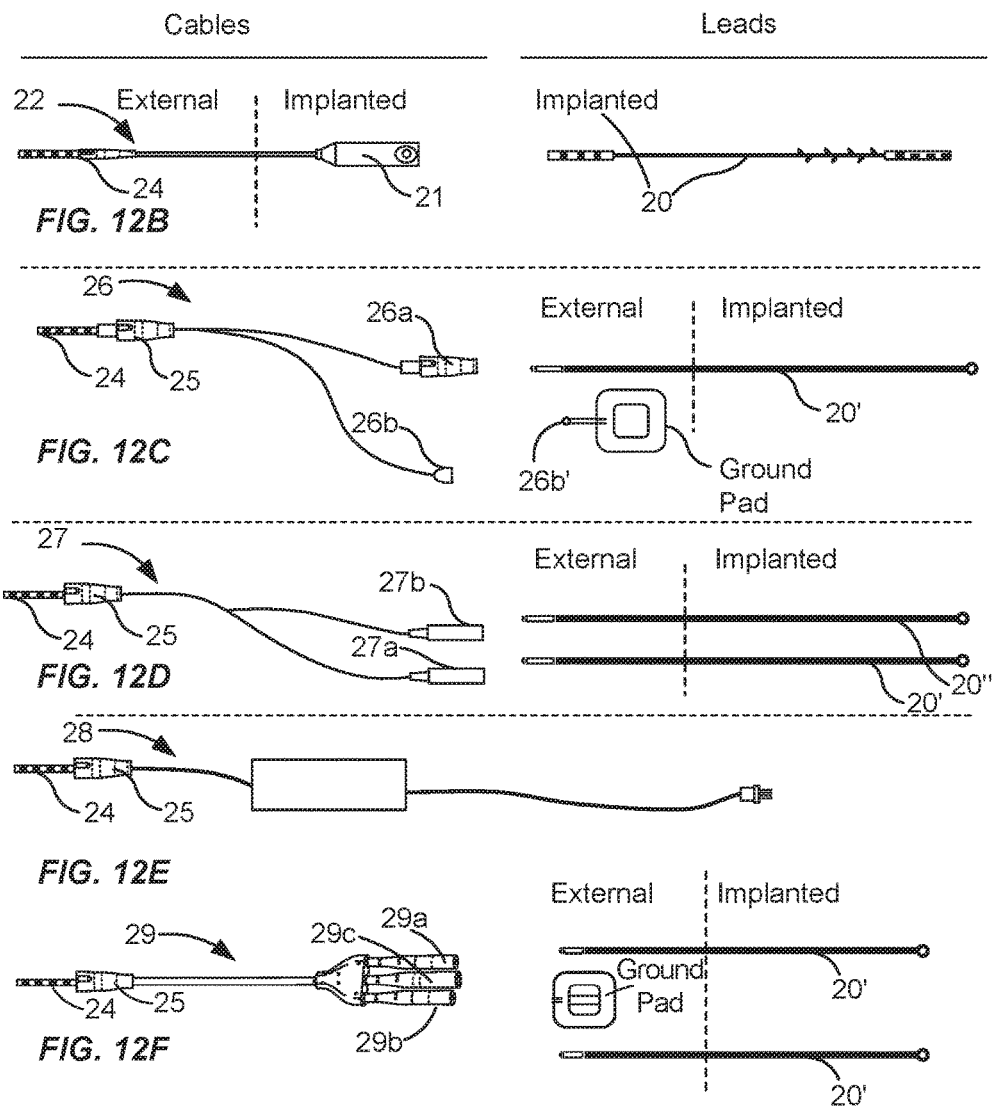
FIGS. 12A-12F illustrate an example EPG and alternate connector cables adapted for varying uses in accordance with some embodiments.

In another aspect, trial system 100 can include differing connector cable sets for use with EPG 40 having a multi-purpose connector receptacle, such as that shown in FIG. 12A. It is appreciated that these cables could also be used with various other EPG devices, such as EPG 50, by use of an adapter or lead extension cable. These differing connector cable sets can include any of those depicted in the examples shown in FIGS. 12B-12F, or various other configuration as desired.

FIG. 12B depicts a lead extension 22, which includes a proximal lead connector 24 similar or identical to that on the implantable neurostimulation lead 20 and an implantable lead connector receptacle 21, which can be connected to a proximal lead connector 24 of a fully implanted neurostimulation lead 20. Such a lead extension can be useful as it allows a neurostimulation lead of a length suitable for permanent implantation to be used during the trial period and remain implanted if converted to a permanent neurostimulation system.

FIG. 12C depicts a grounded neurostimulation therapy cable set 26, which includes a proximal lead connector 24 and boot 25 that is connected in parallel to an external connector receptacle 26a and a ground connector 26b, which can be coupled to a ground pad applied to the patient's skin. Ground connector 26 can be an alligator or J-clip that can be attached to an adhesive ground pad, while the external connector receptacle 26a can be attached to a neurostimulation device 20' having one or more neurostimulation leads.

FIG. 12D depicts a dual neurostimulation lead cable set 27, which includes a proximal lead connector 24 and boot 25 that is connected in parallel to two neurostimulation lead proximal connectors 27a, 27b, which can be identical or different. For example, each electrical contact of the lead connector receptacle 24 can be electrically connected to a corresponding contact within the lead connectors 27a, 27b such that two identical neurostimulation leads can be coupled thereto and receive parallel stimulations along corresponding neurostimulation electrodes or be used as a bipolar pair. In other embodiments, the proximal lead connectors 27a, 27b can be configured differently, for example, each electrical contact within lead connector 27a, 27b can be electrically connected to a dedicated electrical contact within connector receptacle 24 such that two leads 20', 20" can simultaneously deliver differing neurostimulation stimulations. It is further appreciated that such a cable set could be modified for connection of additional neurostimulation leads or devices (e.g. three or more leads).

FIG. 12E depicts a charging cable set 28, which includes a proximal lead connector 24 and boot 25 coupled with a charging cord, which can be connected to a power adapter and plugged directly into an external power source, such as a standard wall outlet. In some embodiments, lead connector 24 could be included as an adapter and used with the same power cord as is used to charge the CP and external charger of the IPG FIG. 12F depicts a multi-lead cable set 29, which includes a proximal lead connector 24 and boot 25 that is connected in parallel to two neurostimulation lead proximal connectors 29a, 29b, which can be identical or different. For example, each electrical contact of the lead connector receptacle 24 can be electrically connected to a corresponding contact within the lead connectors 29a, 29b such that two identical neurostimulation leads can be coupled thereto and receive parallel stimulations along corresponding neurostimulation electrodes or be used as a bipolar pair. In other embodiments, the proximal lead connectors 29a, 29b can be configured differently, for example, each electrical contact within lead connector 29a, 29b can be electrically connected to a dedicated electrical contact within connector receptacle 24 such that two leads 20', 20" can simultaneously deliver differing neurostimulation stimulations. It is further appreciated that such a cable set could be modified for connection of additional neurostimulation leads or devices (e.g. three or more leads). Ground connector 29c is configured to couple with a ground pad affixed externally on the patient.

Figure 13:
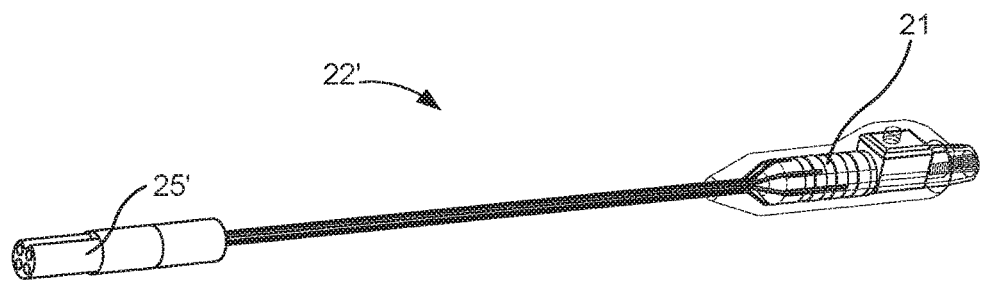
FIG. 13 illustrates an alternative percutaneous extension cable in accordance with some embodiments.

FIG. 13 illustrates an alternative percutaneous extension cable 22' electrically connecting a multi-pin receptacle connector 25' to a proximal lead connector 21, which can be connected to a proximal lead connector 24 of a trial neurostimulation lead or a fully implanted neurostimulation lead 20. Multi-pin receptacle connector 25' is configured to connect with a multi-pin plug connector, for example lead connector 53 of EPG 50. This cable set is particularly useful for use in an advanced trial (e.g. with a tined lead) in which the lead connector 21 is implanted and the tined lead remains implanted when the trial system is converted to a permanently implanted system.

Figure 14:
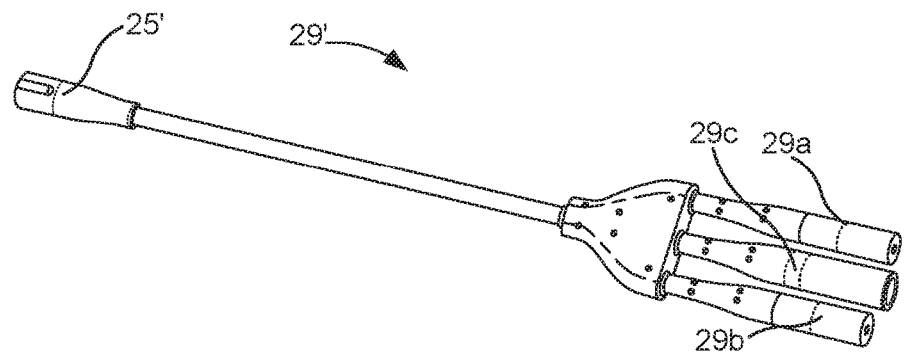
FIG. 14 illustrates an alternative basic trial cable in accordance with some embodiments.

FIG. 14 illustrates an alternative multi-lead cable set 29', which includes a multi-pin receptacle connector 25' that is connected in parallel to two neurostimulation lead proximal connectors 29a, 29b, which can be identical or different. Multi-pin receptacle connector 25' is configured to connect with a multi-pin plug connector, for example lead connector 53 of EPG 50. It is appreciated that multiple leads can be electrically connected to the multi-pin receptacle connector 25' according to various configurations. For example, each electrical contact of the lead connector 25' can be electrically connected to a corresponding contact within the lead connectors 29a, 29b such that two identical neurostimulation leads can be coupled thereto and receive parallel stimulations along corresponding neurostimulation electrodes or be used as a bipolar pair. In other embodiments, the proximal lead connectors 29a, 29b can be configured differently, for example, each electrical contact within lead connector 29a, 29b can be electrically connected to a dedicated electrical contact within lead connector 25' such that two leads 20', 20" can simultaneously deliver differing neurostimulation stimulations. It is further appreciated that such a cable set could be modified for connection of additional neurostimulation leads or devices (e.g. three or more leads). Ground connector 29c is configured to couple with a ground pad affixed externally on the patient. This connector set is more suited for a basic trial, such as a PNE trial.

Figure 15:
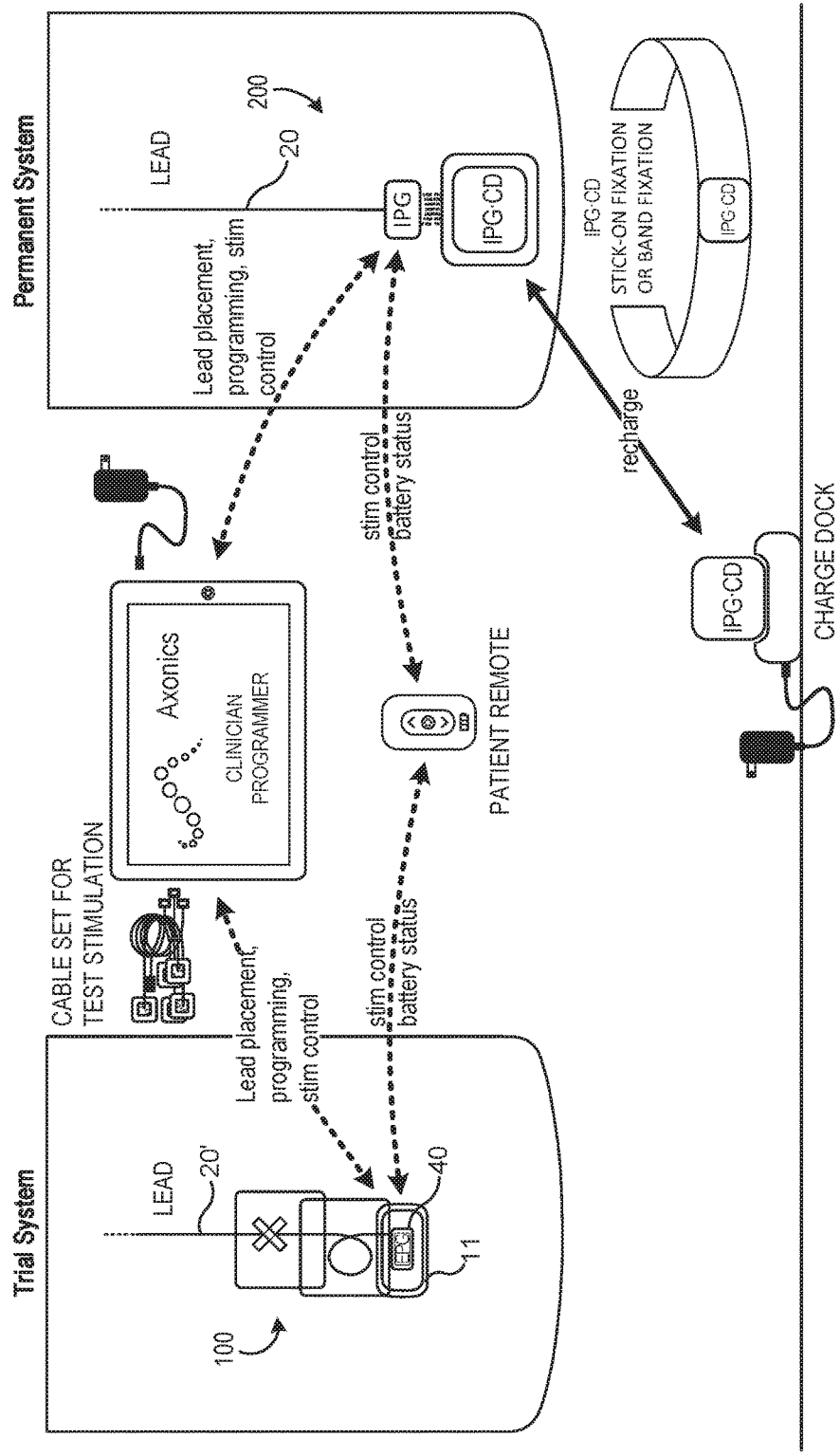
FIG. 15 schematically illustrates a use of a trial neurostimulation system utilizing an EPG affixation device in accordance with some embodiments.

FIG. 15 illustrates a schematic of a trial system 100, in accordance with aspect of the invention, and a permanent system 200. As can be seen, each of the trial and permanent system are compatible for use with a wireless clinician programmer and a patient remote. The communication unit by which EPG wirelessly communicates with the clinician programmer and patient remote can utilize MedRadio or Bluetooth capability, which can provide a communication range of about two meters. The clinician programmer can be used in lead placement, programming and stimulation control in each of the trial and permanent systems. In addition, each allows the patient to control stimulation or monitor battery status with the patient remote. This configuration is advantageous as it allows for an almost seamless transition between the trial system and the permanent system. From the patient's viewpoint, the systems will operate in the same manner and be controlled in the same manner, such that the patient's subjective experience in using the trial system more closely matches what would be experienced in using the permanently implanted system. Thus, this configuration reduces any uncertainties the patient may have as to how the system will operate and be controlled such that the patient will be more likely to convert a trial system to a permanent system.

Figure 16:
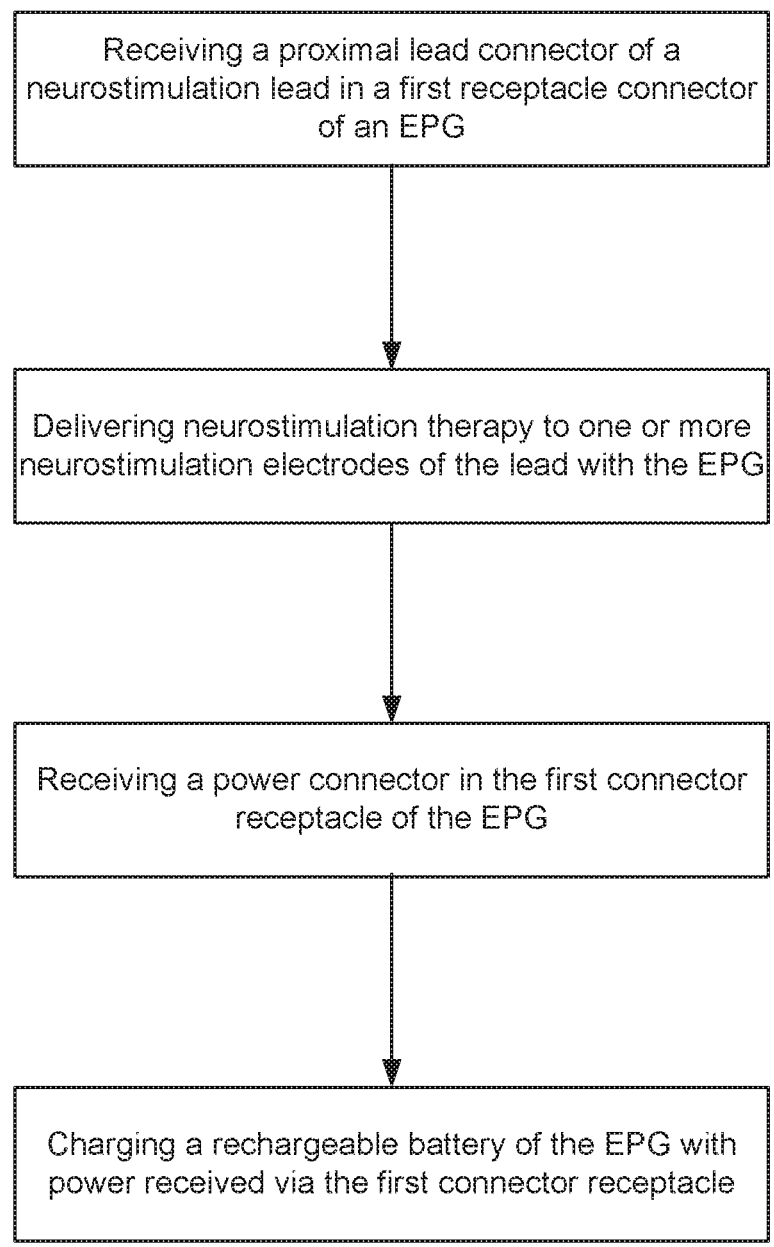
FIGS. 16-17 illustrate methods of performing a trial neurostimulation therapy in accordance with some embodiments.
Figure 17:
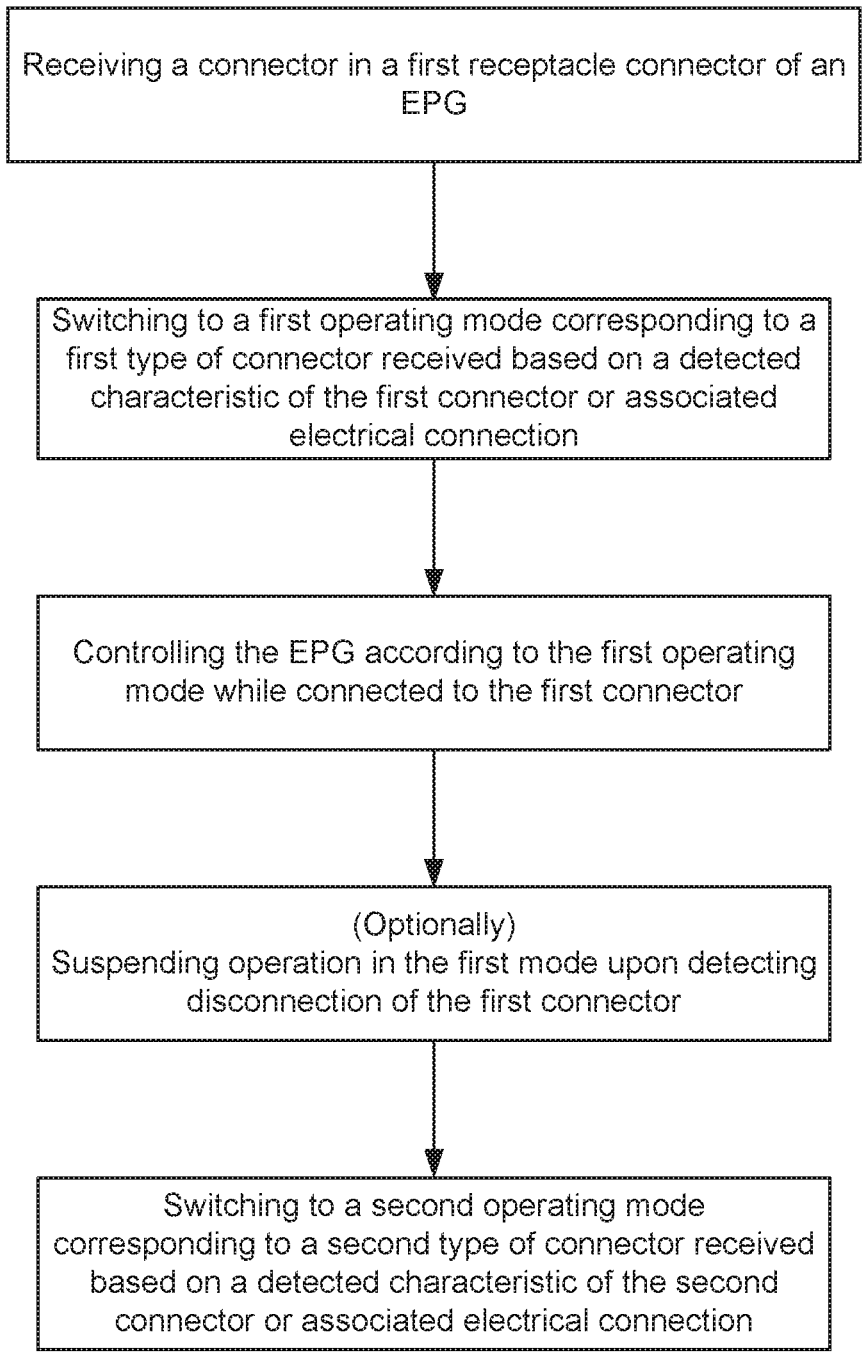

FIGS. 16-17 illustrate methods of controlling operation of an EPG having a multi-purpose port in accordance with aspects of the invention. The method of FIG. 16 includes steps of: receiving a proximal lead connector of a neurostimulation lead in a first connector receptacle of an EPG; delivering neurostimulation therapy to one or more neurostimulation electrodes of the lead with the EPG; receiving a power connector in the first connector receptacle of the EPG; and charging a rechargeable battery of the EPG with power received via the first connector receptacle. The method of FIG. 17 includes steps of: receiving connector in a first connector receptacle of an EPG; switching to a first operating mode corresponding to a first type of connector received based on a detected characteristic of the first connector or associated electrical connection; controlling the EPG according to the first operating mode while connected to the first connector; optionally, suspending operation in the first mode upon detecting disconnection of the first connector; and switching to a second operating mode corresponding to a second type of connector received based on a detected characteristic of the second connector or associated electrical connection. Such operating modes can include but are not limited to a therapy mode corresponding to a proximal lead connector of a trial neurostimulation lead and a charging mode corresponding to a power connector coupled with a power source. It is appreciated that such methods can further include various other types of operating modes that correspond to various other types of connectors and connections as desired.

It is appreciated that other embodiments of the affixation device could include similar releasable mounting feature on a support substrate that allows the EPG to be readily detached by the patient. For example, the mounting features described above could be incorporated into a belt worn, a holster worn around a mid-section of the patient, or worn around the neck similar to a neck badge.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:
1. An external pulse generator comprising:
   a pulse generator electrically configured for generating neurostimulation pulses along a plurality of stimulation channels;
   a battery electrically coupled to the pulse generator;
   an outer housing enclosing the pulse generator and battery;
   an external cable extending from the housing; and
   a multi-pin connector electrically coupleable to the pulse generator through the external cable, wherein a plurality of pins of the multi-pin connector correspond to the plurality of stimulation channels; and an actuatable user interface feature disposed on the housing and configured for initiating wireless communication with an external programmer when actuated
   wherein the actuatable user interface is configured such that:
   actuation while the pulse generator is off or in a hibernation state causes the external pulse generator to be receptive to wireless communication with the external programmer for a pre-determined period of time; and
   wherein operation or communication by the external pulse generator remains unchanged when actuation occurs while the pulse generator is operating or communicating.
2. The external pulse generator of claim 1, wherein the external cable is permanently attached to the housing such that any electrical connections between the multi-pin connector and the pulse generator are permanently sealed.

3. The external pulse generator of claim 1, wherein the external cable is between 1 inch and 12 inches in length.

4. The external pulse generator of claim 1, wherein the battery is non-removable by the patient.

5. The external pulse generator of claim 1, wherein the battery is non-rechargeable.

6. The external pulse generator of claim 1, wherein the actuatable user interface comprises a button or switch.

7. The external pulse generator of claim 1, wherein the external pulse generator is configured such that if no communication is established with the external programmer during the pre-determined period of time, the external pulse generator returns to an off or hibernation state.

8. The external pulse generator of claim 1, wherein the external pulse generator is wirelessly coupleable with a patient remote and configured to turn off stimulation during operation in response to a command received from the patient remote.

9. The external pulse generator of claim 1, further comprising:
   a status indicator interface disposed on the housing and configured to indicate status of: a communication between the external pulse generator and an external programmer, an operating state, a battery level, an error state, or any combination thereof.

10. The external pulse generator of claim 9, wherein the housing comprises opposing major faces, a contoured top surface and a flattened underside surface for placement against the patient when the external pulse generator is worn during a trial period,
   wherein the status indicator interface and the actuatable user interface are disposed on the underside surface of the housing of the external pulse generator.

11. The external pulse generator of claim 1, further comprising:
   a plurality of connectors selectively coupleable within the multi-pin connector, the plurality of connectors including at least two of:
      a first connector on a proximal portion of a neurostimulation lead,
      a second connector coupled in parallel to each of a ground and one or more proximal connectors of one or more implantable neurostimulation leads, each lead having one or more neurostimulation electrodes on a distal portion thereof, and
      a third connector coupled in parallel to two or more proximal connectors of two or more neurostimulation leads.

12. The external pulse generator of claim 1, further comprising:
   one or more connector cables coupleable with the multi-pin connector and one or more neurostimulation leads.

13. The external pulse generator of claim 12, wherein the one or more connectors comprise a lead extension cable extending between a corresponding multi-pin connector and at least one implantable lead connector having a receptacle configured for receiving a proximal lead connector of a fully implantable neurostimulation lead.

14. The external pulse generator of claim 12, wherein the one or more connectors comprise a multi-lead extension cable extending between a corresponding multi-pin connector and a plurality of lead connectors, each having a lead receptacle for coupling with a neurostimulation lead, and at least one ground connector for coupling with a ground patch.

15. The external pulse generator of claim 1 wherein the battery is non-rechargeable and non-removable by the patient, wherein the battery is single-use power source having sufficient power for operation of the EPG for at least the duration of a trial period.

16. The external pulse generator of claim 15, wherein the external pulse generator is configured for use with both a temporary lead having one electrode and a lead having a plurality of electrodes for a trial or permanent implantation.

17. The external pulse generator of claim 1, wherein the external pulse generator is configured for use with both a temporary lead having one electrode and a lead having a plurality of electrodes for a trial or permanent implantation.

18. An external pulse generator comprising:
   a pulse generator electrically configured for generating neurostimulation pulses along a plurality of stimulation channels;
   a battery electrically coupled to the pulse generator;
   an outer housing enclosing the pulse generator and battery;
   a multi-pin connector electrically coupled to the pulse generator, wherein a plurality of pins of the multi-pin connector correspond to the plurality of stimulation channels; and
   an actuatable user interface feature disposed on the housing and configured for initiating wireless communication with an external programmer when actuated, wherein the user interface is further configured such that:
      actuation while the pulse generator is off or in a hibernation state causes the external pulse generator to be receptive to wireless communication with the external programmer for a pre-determined period of time; and
      wherein neurostimulation operation of the external pulse generator remains unchanged when actuation occurs while the pulse generator is operating for neurostimulation.

19. The external pulse generator of claim 18, where the housing comprises opposing major faces, a contoured top surface and a flattened underside surface for placement against the patient when the external pulse generator is worn during a trial period,
   wherein the actuatable user interface is disposed on the underside surface of the housing of the external pulse generator that faces toward the patient when worn.

20. The external pulse generator of claim 18, wherein the external pulse generator includes a single button, the single button being the actuatable user interface feature.

21. The external pulse generator of claim 18, further comprising:
   an external lead extension cable electrically connected and proximally coupled to the pulse generator via the multi-pin connector, wherein the external lead extension cable comprises a distal connector portion having distal connectors for electrically connecting, in parallel, to each of a ground pad for application to a skin of a patient and one or more proximal connectors of one or more implantable neurostimulation leads, each lead having one or more neurostimulation electrodes on a distal portion thereof.

22. The external pulse generator of claim 21, wherein the distal connector portion of the external lead extension cable comprises two distal lead connectors, each configured for coupling with a proximal connector of an implantable neurostimulation lead having one or more neurostimulation electrodes and a distal ground connector configured for coupling with the ground pad applied to the skin of the patient.

23. The external pulse generator of claim 21, wherein the external pulse generator is configured for use with both a temporary lead having one electrode and a lead having a plurality of electrodes for a trial or permanent implantation.

24. The external pulse generator of claim 18, wherein the external pulse generator is configured for use with both a temporary lead having one electrode and a lead having a plurality of electrodes for a trial or permanent implantation.

* * * * *